US012806201B2

(12) United States Patent
Van Den Bosch et al.

(10) Patent No.: US 12,806,201 B2
(45) Date of Patent: Nov. 24, 2026

(54) NEK6 INHIBITION TO TREAT ALS AND FTD

(71) Applicants: VIB VZW, Ghent (BE); KATHOLIEKE UNIVERSITEIT LEUVEN, K.U.LEUVEN R&D, Leuven (BE)

(72) Inventors: Ludo Van Den Bosch, Arendonk (BE); Wenting Guo, Leuven (BE); Catherine Verfaillie, Leuven (BE)

(73) Assignees: VIB VZW, Ghent (BE); Katholieke Universiteit Leuven, K.U. Leuven R&D, Leuven (BE)

( * ) Notice: Subject to any disclaimer, the term of this patent is extended or adjusted under 35 U.S.C. 154(b) by 1191 days.

(21) Appl. No.: 17/702,381

(22) Filed: Mar. 23, 2022

(65) Prior Publication Data

US 2022/0313697 A1 Oct. 6, 2022

Related U.S. Application Data

(63) Continuation of application No. PCT/EP2021/057516, filed on Mar. 24, 2021.

(51) Int. Cl.

| | |
|---|---|
| ***A61K 31/519*** | (2006.01) |
| ***A61K 31/136*** | (2006.01) |
| ***A61K 31/235*** | (2006.01) |
| ***A61K 31/343*** | (2006.01) |
| ***A61K 31/352*** | (2006.01) |
| ***A61K 31/423*** | (2006.01) |
| ***A61K 31/7088*** | (2006.01) |

(52) U.S. Cl.

CPC .......... *A61K 31/519* (2013.01); *A61K 31/136* (2013.01); *A61K 31/235* (2013.01); *A61K 31/343* (2013.01); *A61K 31/352* (2013.01); *A61K 31/423* (2013.01); *A61K 31/7088* (2013.01)

(58) Field of Classification Search

None

See application file for complete search history.

(56) References Cited

FOREIGN PATENT DOCUMENTS

WO 2019126696 A1 6/2019

OTHER PUBLICATIONS

Byrne et al., Lancet Neurol 2012; 11:232-40, published online Feb. 3, 2012 (Year: 2012).*
Glant et al., Arthritis Rheum. Jul. 2013;65(7):1725-35 (Year: 2013).*
He et al., (Pathology-Research and Practice 214 (2018) 1648-1654 (Year: 2018).*
DeJesus-Hernandez et al., (Neuron 72, 245-256, Oct. 20, 2011 (Year: 2011).*
Hinchcliffe et al., Degenerative Neurological and Neuromuscular Disease 2017:7 61-70 (Year: 2017).*
Brenner, David, et al. "NEK1 Mutations in Familial Amyotrophic Lateral Sclerosis." Brain (London, England : 1878), vol. 139, No. Pt 5, 2016, p. e28.
De Donato, Marta, et al. "Identification and Antitumor Activity of a Novel Inhibitor of the NIMA-Related Kinase NEK6." Scientific Reports, vol. 8, No. 1, 2018, pp. 16047-16013.
Kenna, Kevin P, et al. "NEK1 Variants Confer Susceptibility to Amyotrophic Lateral Sclerosis." Nature Genetics, vol. 18, No. 9, 2016, pp. 1037-1042.
PCT International Search Report and Written Opinion; Application No. PCT/EP2021/057516 VIB VZW, International filing date of Mar. 24, 2021, date of mailing Feb. 18, 2022, 14 pages.
Peres De Oliveira, Andressa, et al. "Checking NEKs: Overcoming a Bottleneck in Human Diseases." Molecules (Basel, Switzerland), vol. 25, No. 8, 2020, p. 1778.
Watanabe, Yasuaki, et al. "An Amyotrophic Lateral Sclerosis-Associated Mutant of C21ORF2 Is Stabilized by NEK1-Mediated Hyperphosphorylation and the Inability to Bind FBXO3." IScience, vol. 23, No. 9, 2020, p. 101491.

* cited by examiner

*Primary Examiner* — Evelyn Y Pyla
*Assistant Examiner* — E. Y Pyla
(74) *Attorney, Agent, or Firm* — Patent Law Works LLP

(57) ABSTRACT

The present invention relates to the field of neurological diseases, particularly to neurodegenerative diseases caused by dipeptide repeat toxicity. The invention provides genetic and chemical inhibitors of the protein kinase NEK6 to treat amyotrophic lateral sclerosis and frontotemporal dementia.

9 Claims, 6 Drawing Sheets
(6 of 6 Drawing Sheet(s) Filed in Color)

Specification includes a Sequence Listing.

NEK6 INHIBITION TO TREAT ALS AND FTD

CROSS REFERENCE TO RELATED APPLICATIONS

This application is a continuation of International Patent Application PCT/EP2021/057516, filed Mar. 24, 2021, and entitled "NEK6 Inhibition to Treat ALS and FTD," the entireties of which are hereby incorporated by reference.

FIELD OF THE INVENTION

The present invention relates to the field of neurological diseases, particularly to neurodegenerative diseases caused by dipeptide repeat toxicity. The invention provides genetic and chemical inhibitors of the protein kinase NEK6 to treat amyotrophic lateral sclerosis and frontotemporal dementia.

BACKGROUND

Amyotrophic lateral sclerosis (ALS) and frontotemporal dementia (FTD) are both adult-onset neurodegenerative diseases caused by progressive neuron loss in the brain. While ALS mainly but not exclusively affects motor neurons and is characterized by progressive muscle weakness, atrophy and spasticity, FTD is most known from its deteriorating effect on behaviour, personality and ability to speak and comprehend language. Because of these distinct clinical symptoms they have been long treated as two independent disorders. However, there is increasing evidence that both diseases share neurodegenerative pathways and may be part of a common spectrum.

Over the past decade, more than 50 genes have been associated with ALS and FTD (Mejzini et al Front Neurosci 13:1310; Pottier et al 2016 J Neurochem 138suppl1:32-53; Alsultan et al 2016 Degener Neurol Neuromuscul Dis 6:49-64). Mutations in at least 44 loci have been linked to ALS (Volk et al 2018 Med Genet 30(2):252-258), and correspondingly, at least 14 loci have been linked to FTD (Woollacott et al 2016 J Neurochem 138 (Suppl 1):6-31; Sirkis et al 2019 Curr Genet Med Rep 7(1):41-52; Olszewska et al 2016 Curr Neurol Neurosci Rep 16(12):107). At present, the four major ALS-associated genes are the chromosome 9 open reading frame 72 (C90RF72) (DeJesus-Hernandez et al 2011 Neuron 72(2):245-256; Renton et al 2011 Neuron 72(2):257-268), Cu—Zn superoxide dismutase 1 (SOD1) (Rosen et al 1993 Nature 362(6415):59-62), TAR DNA-binding protein 43 (TARDBP) (Arai et al 2006 Biochem Biophys Res Commun 351(3):602-611; Neumann et al 2006 Science 314(5796):130-133), and fusion in malignant liposarcoma/translocation in liposarcoma (FUS/TLS) (Kwiatkowski et al 2009 Science 323(5918):1205-1208; Vance et al 2009 Science 323(5918):1208-1211). On the other hand, 60% of familial FTD cases originate from mutations in three main genes, i.e. MAPT, GRN and C90RF72.

The C9orf72 mutation is the most common known genetic cause for ALS and FTD (DeJesus-Hernandez et al 2011 Neuron 72:245-256). The C9orf72 mutation is a hexanucleotide repeat expansion of the six letter string of nucleotides GGGGCC (G4C2) (Khan et al 2011 J Neurol Neurosur Psychiatry 83:358-364). This G4C2 repeat expansion accounts for ~40% familial cases and ~7% sporadic cases of ALS and for 18% familial and 6% sporadic cases of FTD in the European population (Majounie et al 2012 Lancet Neurol 11; DeJesus-Hernandez et al 2011 Neuron 72). In most people, the G4C2 repeat length is 2, but in people with C9FTD/ALS—the collective term for C9orf72-associated diseases with clinical features of FTD, ALS or both—hundreds to thousands of repeats may be observed (Balendra and Isaacs 2018 Nat Rev Neurol 14:544-558). It has been recently demonstrated that intermediate expansions of the order of 20 to 30 repeats in size are also associated with ALS (Iacoangeli et al 2019 Acta Neuropathologica Communications 7). The expanded G4C2 repeats are bidirectionally transcribed into repetitive RNA, which forms sense and antisense RNA foci. Remarkably, despite being within a non-coding region of C9orf72, these repetitive RNAs can be translated in every reading frame to form five different dipeptide repeat proteins (DPRs): poly-GA (glycine/alanine), poly-GP (glycine/proline), poly-GR (glycine/arginine), poly-PA (proline/alanine) and poly-PR (proline/arginine), of which at least three are known to be toxic and contribute to neurodegeneration, i.e. poly-PR, poly-GR and poly-GA (van Blitterswijk et al 2013 Neurology 8: 1332-1341).

Since there is still no cure available for neither ALS or FTD, efforts should be done to unravel the pathways and the molecular defects behind the ALS/FTD mutations that lead to these devastating diseases.

SUMMARY

In one aspect, the invention relates to a NEK6 inhibitor for use as a medicament. In particular, it relates to a NEK6 inhibitor for use in (a method for) treating or inhibiting progression of a disorder related to or linked with or caused by dipeptide repeat toxicity or for use in (a method for) treating or inhibiting a symptom of such a disorder. The invention also provides a NEK6 inhibitor for use in reducing or treating axonal transport defects in a subject's neurons. In a particular embodiment, said axonal transport defect is associated with or caused by dipeptide repeat toxicity. In another particular embodiment, a NEK6 inhibitor is provided for use to treat ALS, FTD and/or ALS with FTD. In one embodiment, the NEK6 inhibitor can be specified as an inhibitor specific to NEK6. In another embodiment, the NEK6 inhibitor statistically significantly reduces the expression of NEK6 compared to a control situation in the absence of the inhibitor. In a further particular embodiment, said NEK6 inhibitor is an oligonucleotide, more particularly an RNA silencing agent and even further specified as an inhibitor selected from the group consisting of a siRNA, shRNA, dsRNA, divalent siRNA (di-siRNA), antisense oligonucleotide (ASO), gapmer, microRNA, ribozyme, DNAzyme, nucleic acid aptamer, locked nucleic acid (LNA), bridged nucleic acid (BNA), ethyl bridged nucleic acid (ENA), peptide nucleic acid (PNA) and morpholino oligonucleotide.

In another embodiment, the NEK6 inhibitor of the invention is a nuclease or comprises a nuclease. More particularly, the inhibitor is a CRISPR-Cas, a TALEN, a meganuclease or a Zinc-finger nuclease.

In yet another embodiment, the NEK6 inhibitor of the invention and provided for use according to the invention is selected from an antibody or a fragment thereof binding to NEK6, an alpha-body, a single domain antibody, an intrabody, an aptamer, a DARPin, an affibody, an affitin, an anticalin or a monobody. In yet another embodiment, the NEK6 inhibitor herein disclosed is a small compound and selected from the list consisting of ZINCO5007751, ZINC04384801 and any of the NEK6 inhibitors I-1 to I-33 as described in WO2019126696A1 (which is incorporated by reference herein in its entirety).

In a second aspect, the application provides NEK1 and/or NEK6 for use as a biomarker for ALS and/or FTD caused by C9orf72 repeat expansions. Or alternatively phrased, a method of diagnosing a subject with C9FTD/ALS more particularly with ALS and/or FTD caused by the C9orf72 mutation is provided, comprising the steps of determining the expression level of NEK1 and/or NEK6 in a sample obtained from the subject; comparing said expression level with that from a control sample; diagnosing the test subject with C9FTD/ALS more particularly with C9orf72-ALS and/or C9orf72-FTD when the NEK1 and/or NEK6 expression in the sample of the subject is significantly higher than that in the control sample. In one embodiment, said sample is a blood, serum or plasma sample. In another embodiment, the method further comprises applying an ALS treatment to the subject when the detected expression level of NEK1 and/or NEK6 is significantly higher than that of the control sample.

BRIEF DESCRIPTION OF THE FIGURES

The patent or application file contains at least one drawing executed in color. Copies of this patent or patent application publication with color drawing(s) will be provided by the Office upon request and payment of the necessary fee.

Figure 1:
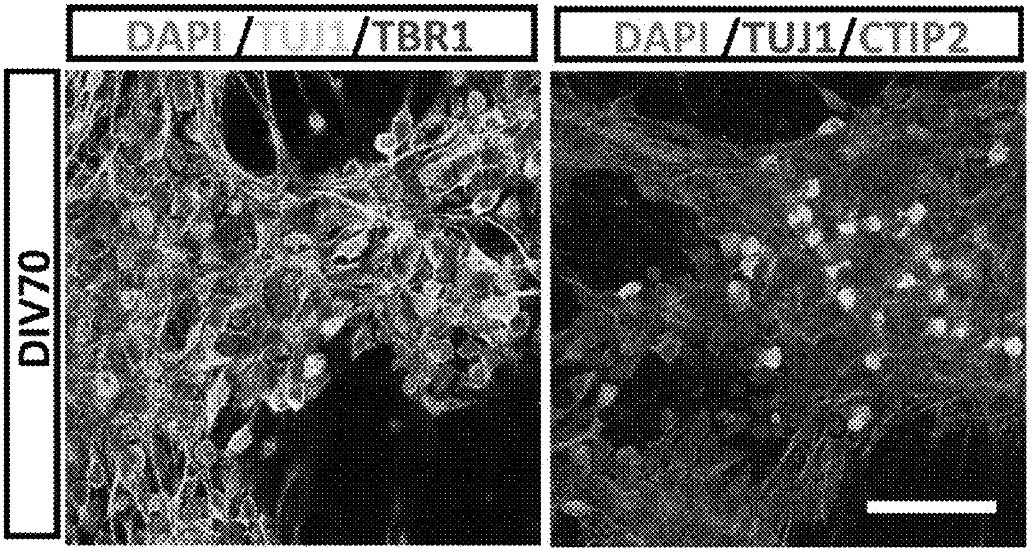
FIG. 1 shows a staining of DIV80 PSC-cortical neuronal progenitor cells for different cortical neuron markers (T-Box Brain Transcription Factor 1 (TBR1), CTIP2 (or BCL11B), neuron tubulin marker TUJ1 and DAPI).

*, *, ** represent p-values of 0.05, 0.001, 0.0001 respectively. Data values represent mean±SEM, ns=not significant.

DETAILED DESCRIPTION

Definitions

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. Where the term “comprising” is used in the present description and claims, it does not exclude other elements or steps. Where an indefinite or definite article is used when referring to a singular noun e.g. “a” or “an”, “the”, this includes a plural of that noun unless something else is specifically stated. Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein. The following terms or definitions are provided solely to aid in the understanding of the invention. Unless specifically defined herein, all terms used herein have the same meaning as they would to one skilled in the art of the present invention. Practitioners are particularly directed to Sambrook et al., Molecular Cloning: A Laboratory Manual, 4th ed., Cold Spring Harbor Press, Plainsview, New York (2012); and Ausubel et al., current Protocols in Molecular Biology (Supplement 100), John Wiley & Sons, New York (2012), for definitions and terms of the art. The definitions provided herein should not be construed to have a scope less than understood by a person of ordinary skill in the art.

In the application, genes and proteins are named according to the international agreements. Human gene symbols generally are italicised, with all letters in uppercase (e.g. NEK6). Protein designations are the same as the gene symbol, but are not italicised, with all letters in uppercase (e.g. NEK6) (world wide web at genenames.org/about/overview). In mice and rats, gene symbols generally are italicized, with only the first letter in uppercase and the remaining letters in lowercase (e.g. Nek6). Protein designations are the same as the gene symbol, but are not italicised and all are upper case (e.g. NEK6) (world wide web at informatics.jax.org/mgihome/nomen/gene.shtml).

“Treatment” refers to any rate of reduction or retardation of the progress of the disease or disorder compared to the progress or expected progress of the disease or disorder when left untreated. More desirable, the treatment results in no/zero progress of the disease or disorder (i.e. “inhibition” or “inhibition of progression”) or even in any rate of regression of the already developed disease or disorder.

“Reduction” or “reducing” or “reduce” as used herein refers to a statistically significant reduction. More particularly, a statistically significant reduction upon administering the inhibitor of the invention compared to a control situation wherein the inhibitor is not administered. In a particular embodiment, said statistically significant reduction is an at least 10%, 15%, 20%, 25%, 30%, 35%, 40%, 45% or 50% reduction compared to the control situation.

Nek6 Inhibition as Treatment of Axonal Transport Defects

In current application it is disclosed that the protein kinase NEK6 is upregulated in cell lines of patients harbouring the C9orf72 mutation. Interestingly, both genetic and chemical inhibition of NEK6 ameliorate the axonal transport defects characteristic for both ALS and FTD.

NEK6 belongs to the NIMA-related kinase (NEK) family of protein kinases consisting of eleven members in human genome (NEK1 to NEK11). Although their function remains partially unknown, the art supports the hypothesis that some members of NEK family may play a role in mitotic progression. For example NEK2, NEK6, NEK7 and NEK9 have been reported to contribute to the establishment of the microtubule based mitotic spindle (Fry et al 2017 Front Cell Dev Biol 5, 102; Moniz et al 2011 Cell Div 6, 18; Fry et al 2012 J Cell Sci 125, 4423-4433). NEK6 shows the highest similarity to NEK7 (85% identity of the catalytic domain) (Kandli et al 2000 Genomics 68, 187-196). To the best of Applicants' knowledge, NEK6 is implicated in cell cycle control and assumed to play a significant role in tumorigenesis, but NEK6 has never been associated with neurodegenerative diseases.

It is herein disclosed that NEK6 inhibition rescues neuron cell death and reduces axonal transport defects that are induced by dipeptide repeat (DPR) toxicity. In the Examples, distinct NEK6 inhibitors are used in combination with several in vitro and in vivo model systems. Therefore, the invention provides in a first aspect the invention provides a method of reducing or treating axonal transport defects in a subject's neurons comprising the step of administering a NEK6 inhibitor to the subject. More particularly, the invention provides a method of treating axonal transport defects induced by DPR toxicity or of treating axonal transport defects in a subject's neurons wherein the subject is suffering from a disease induced by or related to DPR toxicity. The application also provides a method of treating a subject suffering dipeptide repeat toxicity comprising the administering of a NEK6 inhibitor to the subject.

In one embodiment, the disease induced by (or caused by) or related to (or correlated or associated to) DPR toxicity is a neurological or neurodegenerative disease. The term “neurological diseases” as used in this application are disorders that affect the brain and/or the central and autonomic nervous systems. The neurological disorders that are specifically subject of this invention are amyotrophic lateral sclerosis (ALS), frontotemporal dementia (FTD) or ALS correlated with FTD. Amyotrophic lateral sclerosis (ALS) and Frontotemporal Dementia (FTD) are neurodegenerative disorders, related by deterioration of motor and cognitive functions. Aside from cases with an inherited pathogenic mutation, the causes of the disorders are still largely unknown and no effective treatment currently exists. It has been shown that FTD may coexist with ALS and this overlap occurs at clinical, genetic, and molecular levels. In a particular embodiment, the neurological disorder that is subject of this invention is C9FTD/ALS, more particularly C9orf72-ALS and/or C9orf72-FTD.

“Dipeptide repeat toxicity” or “DPR toxicity” as used in current application refers to cellular toxicity caused by the presence of multiple copies of poly-GA, poly-GP, poly-GR, poly-PA or poly-PR, preferably of poly-GA, poly-GR or poly-PR, wherein multiple copies means that there are at least 10, 15 or 20 copies present in the cell. The presence of high amounts of these dipeptide repeats is particularly caused by the GGGGCC hexanucleotide repeat expansion in the C9orf72 mutation.

NEK6 as used herein refers to NIMA Related Kinase 6, NIMA (Never In Mitosis Gene A)-Related Kinase 6, Serine/Threonine-Protein Kinase Nek6, NimA-Related Protein Kinase 6, Protein Kinase SID6-1512, EC 2.7.11.1 or SID6-1512. In a particular embodiment, NEK6 as used herein is the human serine/threonine protein kinase 6 as depicted in SEQ ID No. 1.

In one embodiment of the first aspect, said inhibitor of NEK6 is an inhibitor of NEK6 expression and/or NEK6 activity. Inhibiting NEK6 expression refers to inhibition at the transcription level and production of a functional NEK6 mRNA (see below). Inhibiting NEK6 activity refers to inhibition at the protein level by inhibiting the optimal function of the NEK6 protein. Non-limiting examples of such inhibitors are chemical compounds, intrabodies, alphabodies, antibodies, VHHs or (heavy chain only) single domain antibodies, phosphatases, kinases. Based on the current state of the art, the skilled person is familiar with how neutralising antibodies can be developed against a protein target. In a particular embodiment, the NEK6 inhibitor herein disclosed is a NEK6 binding agent inhibiting the protein kinase activity of NEK6. In an even more particular embodiment, said NEK6 binding agent is an antibody, particularly a single domain antibody, more particularly a heavy chain only single domain antibody such as a VHH or a VNAR.

In a particular embodiment, said inhibitor of NEK6 is an inhibitor of the functional expression of NEK6. “Functional expression” as used herein, implies the formation of a functional gene product. Hence, an “inhibitor of functional expression” is a synonym for an inhibitor of transcription and/or translation of a particular gene. In particular embodiments, an “inhibitor of functional expression” is an “inhibitor of expression”. In one embodiment, the inhibitor inhibits NEK6 expression directly, particularly by binding to the NEK6 transcript. In another embodiment, the inhibitor is a specific NEK6 inhibitor.

For protein coding genes like NEK6, “functional expression” or “expression” can be deregulated at several levels. First, (functional) expression can be modulated at the RNA level, e.g. by degrading the mRNA before translation can be finalised (see below) or by destabilization of the mRNA (e.g. by UTR variants) so that it is degraded before translation occurs from the transcript. Alternatively, by lack of efficient transcription, e.g. because a mutation introduces a new splicing variant. Second, at the level of the DNA. This can for example be achieved by removing or disrupting the NEK6 gene, or by preventing transcription to take place (in both instances preventing synthesis of the relevant gene product, e.g. NEK6).

Oligonucleotide Inhibitors

A well-established method of interfering with gene expression is based on the inhibitory RNA technology. Said technology, sometimes also referred to as “RNA interference” or “RNAi” is a form of post-transcriptional gene silencing. The inhibitory RNA technology is also used in this application as one of the methods to inhibit or reduce the functional expression of NEK6 (see Example 2).

RNA interference or RNAi is a biological process in which targeted mRNA molecules are neutralised resulting in inhibited gene expression or translation. Originally discovered as a natural occurring intracellular process to remove foreign RNAs (e.g. viral RNAs), RNAi is clinically advanced and can nowadays be initiated on demand to silence the expression of target genes in almost every species including humans.

In certain embodiments, the NEK6 inhibitor is capable of preventing complete processing (e.g. the full translation and/or expression) of a mRNA molecule through a post-transcriptional silencing mechanism. Said inhibitor includes small (<50 bp), noncoding RNA or DNA molecules, for example RNA, DNA or RNA/DNA duplexes comprising paired strands, as well as precursor RNAs from which such small non-coding RNAs can be generated. Exemplary NEK6 inhibitors include siRNAs, shRNAs, miRNAs, siRNA-like duplexes, antisense oligonucleotides, GAPMER molecules, and dual-function oligonucleotides as well as precursors thereof. In one embodiment, the NEK6 inhibitor is capable of inducing RNAi. In another embodiment, the NEK6 inhibitor is capable of mediating translational repression. As used herein, the term “translational repression” refers to a selective inhibition of mRNA translation. Natural translational repression proceeds via miRNAs cleaved from shRNA precursors. Both RNAi and translational repression are mediated by the RISC complex. Both RNAi and translational repression occur naturally or can be initiated on demand, for example, to silence the expression of target genes. Techniques for selecting target sequences for RNAi are well known in the art.

The mediators of sequence-specific messenger RNA degradation are small interfering RNAs (siRNAs) generated by ribonuclease III cleavage from longer dsRNAs. Generally, the length of siRNAs is between 20-25 nucleotides (Elbashir et al 2001 Nature 411: 494-498). The siRNA typically comprise a sense RNA strand and a complementary antisense RNA strand annealed together by standard Watson-Crick base pairing interactions (hereinafter “base paired”). The sense strand comprises a nucleic acid sequence that is identical to a target sequence (e.g. the NEK6 sequence in this application) contained within the target mRNA. The antisense or guide strand is thus complementary to a target transcript. The sense and antisense strands of the present siRNA can comprise two complementary, single stranded RNA molecules or can comprise a single molecule in which two complementary portions are base paired and are covalently linked by a single stranded “hairpin” area (often referred to as shRNA).

siRNA molecules classically consist of a characteristic 19+2mer structure (that is, a duplex of two 21-nucleotide RNA molecules with 19 complementary bases and terminal 2-nucleotide 3' overhangs).

In one embodiment the NEK6 inhibitor herein disclosed is an oligonucleotide. More particularly, an oligonucleotide for inhibiting or silencing gene expression in the process of RNA interference or RNA degradation based reduction of gene expression. The term “oligonucleotide” refers to a short polymer of nucleotides and/or nucleotide analogues. An oligonucleotide as used herein can be single stranded and comprise or consist of DNA or RNA or can be double stranded or partially double stranded and comprise or consist of DNA, RNA or a DNA/RNA hybrid. In a particular embodiment, the NEK6 inhibitor is an antisense oligonucleotide or an RNA oligonucleotide.

In another embodiment, said NEK6 inhibitor is an RNA silencing agent. As used herein, the term “RNA silencing agent” refers to an RNA or DNA molecule or an RNA/DNA molecule, which is capable of inhibiting or “silencing” the expression of a target gene. The oligonucleotide or RNA silencing agent that can be used to inhibit or reduce the functional expression of for example NEK6 can comprise partially purified RNA, substantially pure RNA, synthetic RNA, or recombinantly produced RNA, as well as altered RNA that differs from naturally occurring RNA by the addition, deletion, substitution and/or alteration of one or more nucleotides. Such alterations can include addition of non-nucleotide material, such as to the end(s) of the oligonucleotide or RNA silencing agent or to one or more internal nucleotides of the oligonucleotide or RNA silencing agent, including modifications that make the oligonucleotide or RNA silencing agent resistant to nuclease digestion. The oligonucleotides or RNA silencing agents can be chemically synthesized or recombinantly produced using methods known in the art.

As used herein, the term "antisense strand" of an RNA silencing agent, e.g. an siRNA or RNA silencing agent, refers to a strand that is substantially complementary to a section of about 10-50 nucleotides, e.g. about 15-30, 16-25, 18-23 or 19-22 nucleotides of the mRNA of the gene targeted for silencing. The antisense strand or first strand has sequence sufficiently complementary to the desired target mRNA sequence to direct target-specific silencing, e.g., complementarity sufficient to trigger the destruction of the desired target mRNA by the RNAi machinery or process (RNAi interference) or complementarity sufficient to trigger translational repression of the desired target mRNA.

The term "sense strand" or "second strand" of an RNA silencing agent, e.g. an siRNA or RNA silencing agent, refers to a strand that is complementary to the antisense strand or first strand. Antisense and sense strands can also be referred to as first or second strands, the first or second strand having complementarity to the target sequence and the respective second or first strand having complementarity to said first or second strand. miRNA duplex intermediates or siRNA-like duplexes include a miRNA strand having sufficient complementarity to a section of about 10-50 nucleotides of the mRNA of the gene targeted for silencing and a miRNA* strand having sufficient complementarity to form a duplex with the miRNA strand.

The inhibitor of (functional) expression of NEK6 can also be a single stranded oligonucleotide and thus an antisense molecule or anti-NEK6 agent consisting of or comprising an oligonucleotide of at least about 10 nucleotides in length for which no transcription is needed in the treated subject. Antisense approaches involve the design of oligonucleotides (either DNA or RNA, or derivatives thereof) that are complementary to an RNA encoded by polynucleotide sequences of the NEK6 gene. Antisense RNA may be introduced into a cell to inhibit translation of a complementary mRNA by base pairing to it and physically obstructing the translation machinery. This effect is therefore stoichiometric. Absolute complementarity, although preferred, is not required. A sequence "complementary" to a portion of an RNA, as referred to herein, means a sequence having sufficient complementarity to be able to hybridize with the RNA, forming a stable duplex. The ability to hybridize will depend on both the degree of complementarity and the length of the antisense polynucleotide sequence. Generally, the longer the hybridizing polynucleotide sequence, the more base mismatches with an RNA it may contain and still form a stable duplex. One skilled in the art can ascertain a tolerable degree of mismatch by use of standard procedures to determine the melting point of the hybridized complex. Antisense oligonucleotides should be at least 10 nucleotides in length, and are preferably oligonucleotides ranging from 15 to about 50 nucleotides in length. In certain embodiments, the oligonucleotide is at least 15 nucleotides, at least 18 nucleotides, at least 20 nucleotides, at least 25 nucleotides, at least 30 nucleotides, at least 35 nucleotides, at least 40 nucleotides, or at least 50 nucleotides in length or ranging from 15 to 30, 16 to 25, 18 to 23 or 19 to 22 nucleotides.

Besides siRNAs, other oligonucleotide inhibitors are as suited to inhibit expression or functional expression of NEK6 and thus to be used in the treatment of the diseases related to dipeptide repeat toxicity. A non-limiting list of recent developments in oligonucleotides capable to inhibit the expression of a target gene are explained below. As these are all variations on the same principle of inhibiting gene expression at the RNA level, they all fall within the scope of this application.

Antisense oligonucleotides (ASOs) are small (~18-30 nucleotides), synthetic, single-stranded nucleic acid polymers of diverse chemistries, which can be employed to modulate gene expression via various mechanisms.

Bridged nucleic acids (BNAs) are types of nucleotide in which the pucker of the ribose sugar is constrained in the 3'-endo conformation via a bridge between the 2' and 4' carbon atoms. The most commonly used variations are locked nucleic acid (LNA), 2',4'-constrained 2'-O-ethyl (constrained ethyl) BNA (cEt) and to a lesser extent 2'-O, 4'-C-ethylene-bridged nucleic acid (ENA).

Other alternatives are synthetic structural types such as phosphorothiates, 2'-O-alkylribonucleotide chimeras, locked nucleic acid (LNA), peptide nucleic acid (PNA) or morpholinos. PNAs and morpholinos bind complementary DNA and RNA targets with high affinity and specificity, and act through a simple steric blockade of the RNA translational machinery. Because they appear to be completely resistant to nuclease attack, morpholino oligonucleotides therefore represent an important class of antisense molecule.

Another particular form of antisense RNA strategy are gapmers. A gapmer is a chimeric antisense oligonucleotide that contains a central block of deoxynucleotide monomers sufficiently long to induce RNase H cleavage. The central block of a gapmer is flanked by blocks of 2'-O modified ribonucleotides or other artificially modified ribonucleotide monomers such as bridged nucleic acids (BNAs) that protect the internal block from nuclease degradation. Gapmers have been used to obtain RNase-H mediated cleavage of target RNAs, while reducing the number of phosphorothioate linkages. Phosphorothioates possess increased resistance to nucleases compared to unmodified DNA. By recruiting RNase H, gapmers selectively cleave the targeted oligonucleotide strand. The cleavage of this strand initiates an antisense effect. This approach has proven to be a powerful method in the inhibition of gene functions and is emerging as a popular approach for antisense therapeutics. Gapmers are offered commercially, e.g. LNA longRNA GapmeRs by Exiqon, or MOE gapmers by Isis pharmaceuticals. MOE gapmers or "2'MOE gapmers" are an antisense phosphorothioate oligonucleotide of 15-30 nucleotides wherein all of the backbone linkages are modified by adding a sulfur at the non-bridging oxygen (phosphorothioate) and a stretch of at least 10 consecutive nucleotides remain unmodified (deoxy sugars) and the remaining nucleotides contain an O'-methyl O'-ethyl substitution at the 2' position (MOE).

A very recent RNA silencing agent alternative are divalent siRNAs. Divalent siRNA (di-siRNA) have been shown to support a potent, sustained gene silencing in the central nervous system of mice and non-human primates following a single injection into the cerebrospinal fluid (Alterman et al 2019 Nature Biotech 37, 884-894). Di-siRNAs are composed of two fully chemically modified, phosphorothioate-containing siRNAs connected by a linker.

Other non-limiting examples of oligonucleotide inhibitors are nucleic acid aptamers, ribozymes and deoxyribozymes. Nucleic acid aptamers are short single-stranded DNA- or RNA-based oligonucleotides that can selectively bind to small molecular ligands or protein targets with high affinity and specificity, when folded into their unique three-dimensional structures. They typically have a length in the range of 10-100 nucleotides (Ellington et al 1990 Nature 346:818-822; Tuerk and Gold 1990 Science 249:505-510).

Ribozymes are RNA molecules that have the ability to catalyze specific biochemical reactions, including RNA splicing in gene expression, similar to the action of protein enzymes (Asha et al 2019 J Clin Med 8:6). Since their discovery, these catalytic RNAs have been shown to play a role in several biological processes such as the RNA splicing, RNA processing and the replication of RNA genomes. Ribozymes occur in nature and mainly cleave the phosphodiester bonds of nucleic acids. There are several classes of ribozymes, of which the hammerhead and hairpin ribozymes have received most attention because of their smaller size. The hammerhead ribozyme has a 22-nt-long conserved catalytic core, that target RNA with NUX (in which N is any nucleotide and X any nucleotide except guanosine) sequence, along with two flanked hybridizing arms (complimentary to target RNA). Several studies have utilized the hammerhead ribozymes for catalytically cleaving the target RNA due to its high catalytic activity.

Deoxyribozymes, also known as DNAzymes or DNA enzymes, are synthetic catalytic single-stranded deoxyribonucleic acid molecules that display precise substrate recognition and have the ability to cleave sequence-specific mRNA molecules with greater biological stability (Asha et al 2019 J Clin Med 8:6). A DNAzyme molecule has one central catalytic motif flanked by two arms. Both arms are designed complimentary to the target RNA molecule so that the designed DNAzyme binds to it on a Watson-Crick basis.

Oligonucleotides of the invention may be synthesized by standard methods known in the art. For example, phosphorothioate oligomers may be synthesized by the method of Stein et al. (1988 Nucleic Acids Res 16, 3209-3021), methylphosphonate oligomers can be prepared by use of controlled pore glass polymer supports (Sarin et al 1988 Proc Natl Acad Sci USA 85, 7448-7451) and morpholino oligonucleotides may be synthesized by the method of Summerton and Weller (U.S. Pat. Nos. 5,217,866 and 5,185,444).

Double stranded oligonucleotide inhibitors such as siRNAs can be synthesized as two separate, complementary RNA molecules or as a single RNA molecule with two complementary regions. Commercial suppliers of synthetic RNA molecules or synthesis reagents include Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK).

Hence, to summarize, the NEK6 inhibitor of the invention can be selected from a list of RNA silencing agents that might slightly differ on structural level but all silence the expression of NEK6. This non-limiting list consists of siRNA, shRNA, dsRNA, divalent siRNA (di-siRNA), antisense oligonucleotides (ASO), gapmer, microRNA, ribozyme, DNAzyme, nucleic acid aptamer, locked nucleic acid (LNA), bridged nucleic acid (BNA), ethyl bridged nucleic acid (ENA), peptide nucleic acid (PNA) and morpholino oligonucleotides.

In a particular embodiment of the application, the NEK6 inhibitor herein disclosed is an inhibitor of the inhibitory RNA technology or alternatively phrased an RNA oligomer or an antisense oligomer. In a further embodiment, any of these provided NEK6 inhibitors inhibit the expression of NEK6.

Nuclease-Based Inhibitors

Another way in which gene expression can be deregulated is by use of nuclease activity. This kind of regulation is at the level of the DNA or in specific cases at the RNA level.

Functionality of genes can be knocked out by for example zinc finger nucleases. Zinc-finger nucleases (ZFNs) are artificial restriction enzymes generated by fusing a zinc finger DNA-binding domain to a DNA-cleavage domain. Zinc finger domains can be engineered to target desired DNA sequences, which enable zinc-finger nucleases to target unique sequence within a complex genome. By taking advantage of endogenous DNA repair machinery, these reagents can be used to precisely alter the genomes of higher organisms.

Other technologies for genome customization that can be used to knock out genes are meganucleases and TAL effector nucleases (TALENs, Cellectis bioresearch). A TALEN is composed of a TALE DNA binding domain for sequence-specific recognition fused to the catalytic domain of an endonuclease that introduces double strand breaks (DSB). The DNA binding domain of a TALEN is capable of targeting with high precision a large recognition site (for instance 17 bp).

Meganucleases are sequence-specific endonucleases, naturally occurring "DNA scissors", originating from a variety of single-celled organisms such as bacteria, yeast, algae and some plant organelles. Meganucleases have long recognition sites of between 12 and 30 base pairs. The recognition site of natural meganucleases can be modified in order to target native genomic DNA sequences (such as endogenous genes).

Another recent and very popular genome editing technology is the CRISPR-Cas system, which can be used to achieve RNA-guided genome engineering. CRISPR interference is a genetic technique which allows for sequence-specific control of gene expression in prokaryotic and eukaryotic cells. It is based on the bacterial immune system-derived CRISPR (clustered regularly interspaced palindromic repeats) pathway that confers resistance to foreign genetic elements such as those present within plasmids and phages providing a form of acquired immunity. A simple version of the CRISPR/Cas system, CRISPR/Cas9, has been modified to edit genomes. By delivering the Cas9 nuclease complexed with a synthetic guide RNA (gRNA) into a cell, the cell's genome can be cut at a desired location, allowing existing genes to be removed and/or new ones added (Marraffini and Sontheimer 2010 Nat Rev Genet 11:181-190). In meantime, alternatives for the Cas9 nuclease have been identified, e.g. Cpf1 or Cas12 (Zetsche et al 2015 Cell 3:759-771). Recently, it was demonstrated that the CRISPR-Cas editing system can also be used to target RNA. It has been shown that the Class 2 type VI-A CRISPR-Cas effector C2c2 (also known as Cas13) can be programmed to cleave single stranded RNA targets carrying complementary protospacers (Abudayyet et al 2016 Science aaf5573; Abudayyet et al 2017 Nature 5:280-284). C2c2 is a single-effector endoRNase mediating ssRNA cleavage once it has been guided by a single crRNA guide toward the target RNA. This system can thus also be used to target and thus to break down NEK6 mRNA.

In one particular embodiment, the NEK6 inhibitor disclosed herein is a nuclease-based inhibitor. More particularly, as nuclease-based inhibitor selected from the list consisting of a zinc-finger nuclease, a TALEN, a meganuclease and a CRISPR-Cas nuclease or alternatively phrase an inhibitor of the CRISPR-Cas technology.

DNA Interference

Next to the use of nuclease-based inhibitors to reduce or inhibit functional expression of the NEK6 gene on the level of the DNA, lack of transcription can also be induced by epigenetic changes (e.g. DNA methylation) or by loss-of-function mutations. A "loss-of-function" or "LOF" mutation as used herein is a mutation that prevents, reduces or abolishes the function of a gene product as opposed to a gain-of-function mutation that confers enhanced or new activity on a protein. LOF can be caused by a wide range of mutation types, including, but not limited to, a deletion of the entire gene or part of the gene, splice site mutations, frame-shift mutations caused by small insertions and deletions, nonsense mutations, missense mutations replacing an essential amino acid and mutations preventing correct cellular localization of the product. Also included within this definition are mutations in promoter or regulatory regions of the NEK6 gene if these interfere with gene function. A null mutation is an LOF mutation that completely abolishes the function of the gene product. A null mutation in one allele will typically reduce expression levels by 50%, but may have severe effects on the function of the gene product. Note that functional expression can also be deregulated because of a gain-of-function mutation: by conferring a new activity on the protein, the normal function of the protein is deregulated, and less functionally active protein is expressed. Vice versa, functional expression can be increased e.g. through gene duplication or by lack of DNA methylation.

If inhibition is to be achieved at the DNA level, this may be done using gene therapy to knock-out or disrupt the target gene. As used herein, a "knock-out" can be a gene knock-down or the gene can be knocked out by a mutation such as, a point mutation, an insertion, a deletion, a frameshift, or a missense mutation by techniques known in the art, including, but not limited to, retroviral gene transfer.

Peptide Based Inhibitors

A third way of inhibiting the functional expression of NEK6 is at the protein level by interfering with the function or structure of the NEK6 protein. Interfering with structure, which can also result in inhibition of function, can be achieved by e.g. binding moieties that shield e.g. the binding site on the protein of interest for a ligand of interest. Non-limiting examples are (monoclonal) antibodies or antigen-binding fragments thereof, alpha-bodies, single domain antibodies, VHHs or (heavy chain only) single domain antibodies, nanobodies, intrabodies (i.e. antibodies binding and/or acting to intracellular target; this typically requires the expression of the antibody within the target cell, which can be accomplished by gene therapy), aptamers, DARPins, affibodies, affitins, anticalins, peptide aptamers, monobodies, phosphatases (in case of phosphorylated target) and kinases (in case of a phosphorylatable target).

The term "antibody" as used herein, refers to an immunoglobulin (Ig) molecule or a molecule comprising an immunoglobulin (Ig) domain, which specifically binds with an antigen. "Antibodies" can be intact immunoglobulins derived from natural sources or from recombinant sources and can be immunoreactive portions of intact immunoglobulins.

"Conventional" antibodies comprise two heavy chains linked together by disulfide bonds and two light chains, one light chain being linked to each of the heavy chains by disulfide bonds. Each heavy chain has at one end a variable domain (VH) followed by a number of constant domains (three or four constant domains, CH1, CH2, CH3 and CH4, depending on the antibody class). Each light chain has a variable domain (VL) at one end and a constant domain (CL) at its other end; the constant domains of the light chains each align with the first constant domains of the heavy chains, and the light chain variable domains each align with the variable domains of the heavy chains. Typically, a heavy chain variable domain (VH) and a light chain variable domain (VL) interact to form an antigen binding site.

In contrast to conventional antibodies that bind to the epitope of their respective antigen by a VH-VL pair of immunoglobulin domains, immunoglobulin single variable domains are capable of specifically binding to an epitope of the antigen by a single VH/VHH or VL domain.

A "single variable domain antibody" may be a light chain variable domain sequence (e.g. a VL-sequence) or a suitable fragment thereof; or a heavy chain variable domain sequence (e.g. a VH-sequence or VHH sequence) or a suitable fragment thereof; as long as it is capable of forming a single antigen binding unit. In one embodiment of the invention, the immunoglobulin single variable domains are heavy chain variable domain sequences (e.g. a VHH). VHH antibodies have originally been described as the antigen-binding Ig variable domain of "heavy chain antibodies" (i.e. of "antibodies devoid of light chains"; Hamers-Casterman et al (1993) Nature 363: 446-448). The term "VHH domain" has been chosen to distinguish these variable domains from the heavy chain variable domains that are present in conventional 4-chain antibodies (which are referred to herein as "VH domains") and from the light chain variable domains that are present in conventional 4-chain antibodies (which are referred to herein as "VL domains"). The single domain antibodies typically exist in camels, dromedaries and llamas. But also in the serum of nurse sharks (Ginglymostomatidae) and wobbegong sharks (Orectolobidae), these antibodies have been discovered. Without the light chain, these heavy-chain antibodies bind to their antigens by one single domain, the variable antigen binding domain of the heavy-chain immunoglobulin, referred to as Vab (camelid antibodies) or V-NAR (shark antibodies). These smallest intact and independently functional antigen-binding fragment Vab is referred to as nano-antibody or nanobody (Muyldermans 2001, J Biotechnol 74, 277-302).

In particular embodiments, the single variable domain antibody provided herein is a Nanobody or a suitable fragment thereof. Note: Nanobody®, Nanobodies® and Nanoclone® are registered trademarks of Ablynx N.V. For a further description of VHHs and Nanobody, reference is made to the review article by Muyldermans (Reviews in Molecular Biotechnology 74: 277-302, 2001), as well as to the following patent applications, which are mentioned as general background art: WO 94/04678, WO 95/04079 and WO 96/34103 of the Vrije Universiteit Brussel; WO 94/25591, WO 99/37681, WO 00/40968, WO 00/43507, WO 00/65057, WO 01/40310, WO 01/44301, EP 1134231 and WO 02/48193 of Unilever; WO 97/49805, WO 01/21817, WO 03/035694, WO 03/054016 and WO 03/055527 of the Vlaams Instituut voor Biotechnologie (VIB); WO 03/050531 of Algonomics N.V. and Ablynx N.V.; WO 01/90190 by the National Research Council of Canada; WO 03/025020 (=EP 1433793) by the Institute of Antibodies; as well as WO 04/041867, WO 04/041862, WO 04/041865, WO 04/041863, WO 04/062551, WO 05/044858, WO 06/40153, WO 06/079372, WO 06/122786, WO 06/122787 and WO 06/122825, by Ablynx N.V. and the further published patent applications by Ablynx N.V. As described in these references, Nanobody (in particular VHH sequences and partially humanized Nanobody) can in particular be characterized by the presence of one or more "Hallmark residues" in one or more of the framework sequences. A further description of the Nanobody, including humanization and/or camelization of Nanobody, as well as other modifications, parts or fragments, derivatives or “Nanobody fusions”, multivalent constructs (including some non-limiting examples of linker sequences) and different modifications to increase the half-life of the Nanobody and their preparations can be found e.g. in WO 08/101985 and WO 08/142164.

The term “antibody fragment” refers to any molecule comprising one or more fragments (usually one or more CDRs) of an antibody (the parent antibody) such that it binds to the same antigen to which the parent antibody binds. Antibody fragments include Fv, Fab, Fab', Fab'-SH, single-chain antibody molecules (such as scFv), F(ab') 2, single variable VH domains, and single variable VL domains (Holliger & Hudson 2005, Nature Biotechnol 23, 1126-1136), Vab and V-NAR.

“Alpha-bodies” are also known as cell-penetrating alpha-bodies and are small 10 kDa proteins engineered to bind to a variety of antigens.

“Peptide aptamers” consist of one (or more) short variable peptide domains, attached at both ends to a protein scaffold, e.g. the Affimer scaffold based on the cystatin protein fold. A further variation is described in e.g. WO 2004/077062 wherein e.g. 2 peptide loops are attached to an organic scaffold. Phage-display screening of such peptides has proven to be possible in e.g. WO 2009/098450.

“DARPins” stands for designed ankyrin repeat proteins. DARPin libraries with randomized potential target interaction residues, with diversities of over $10^{12}$ variants, have been generated at the DNA level. From these, DARPins can be selected for binding to a target of choice with picomolar affinity and specificity.

“Affitins”, or nanofitins, are artificial proteins structurally derived from the DNA binding protein Sac7d, found in *Sulfolobus acidocaldarius*. By randomizing the amino acids on the binding surface of Sac7d and subjecting the resulting protein library to rounds of ribosome display, the affinity can be directed towards various targets, such as peptides, proteins, viruses, and bacteria. “Anticalins” are derived from human lipocalins which are a family of naturally binding proteins and mutation of amino acids at the binding site allows for changing the affinity and selectivity towards a target of interest. They have better tissue penetration than antibodies and are stable at temperatures up to 70° C. “Monobodies” are synthetic binding proteins that are constructed starting from the fibronectin type III domain (FN3) as a molecular scaffold.

Based on the above, a NEK6 inhibitor for use in a method according to the invention can be defined as those inhibitors specific to NEK6 including those selected from the group consisting of an antibody or a fragment thereof binding to NEK6, an alpha-body, a nanobody, a single domain antibody, a heavy chain only single domain antibody, an intrabody, an aptamer, a DARPin, an affibody, an affitin, an anticalin, and a monobody. In the above, “specific to NEK6” is referring to the fact that the inhibitor is acting at the level of NEK6 and not at the level of another protein or other neurological factor. Specificity can be ascertained by e.g. determining physical interaction of the inhibitor to NEK6.

Small Molecules

In another embodiment, said inhibitor of NEK6 is a chemical inhibitor or chemical compound. In a particular embodiment, said compound inhibiting NEK6 functional expression and/or activity is ZINCO5007751 (CAS nr. 591239-68-8) or ZINC04384801. Both compounds have been described in De Donato et al (2018 Scientific Reports 8:16047) and in WO2019193494A1 as NEK6 inhibitors and have the following formula:

ZINC05007751

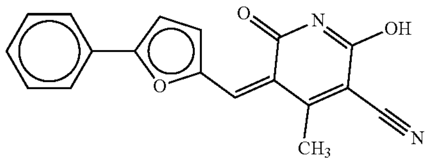

ZINC04384801

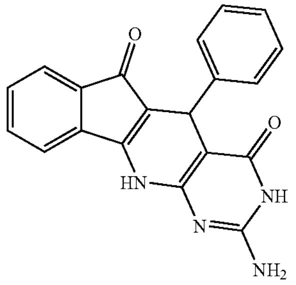

In another particular embodiment, said the NEK6 inhibitor of the invention is a compound selected from the list consisting of compound I-1 to I-24 as described in WO2019126696A1. More particularly, the compound is selected from the following list:

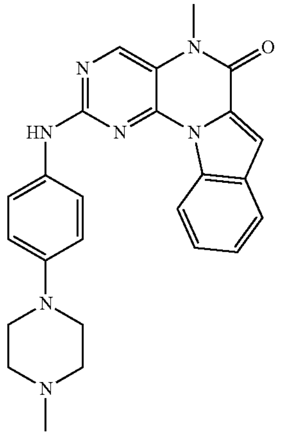

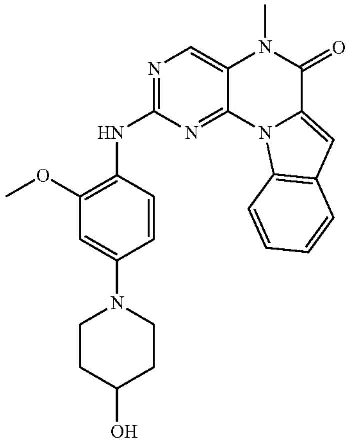

-continued
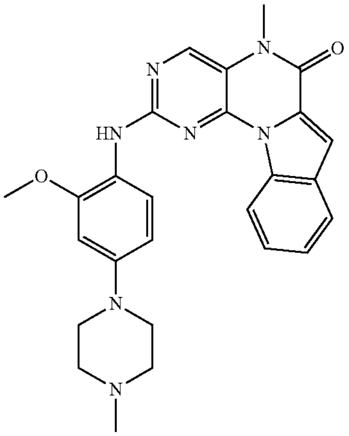
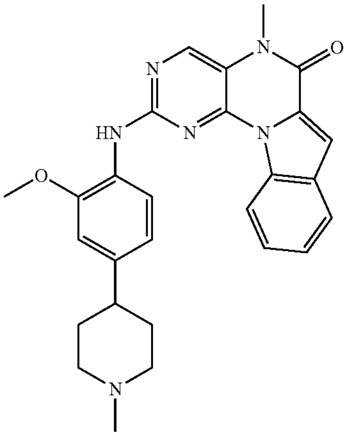
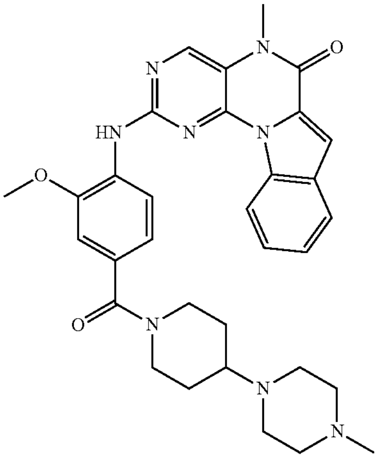
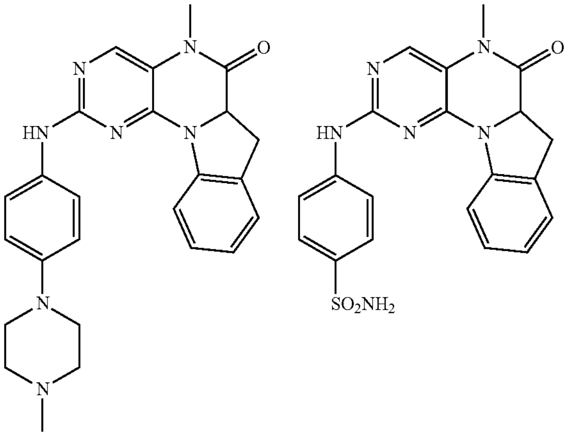
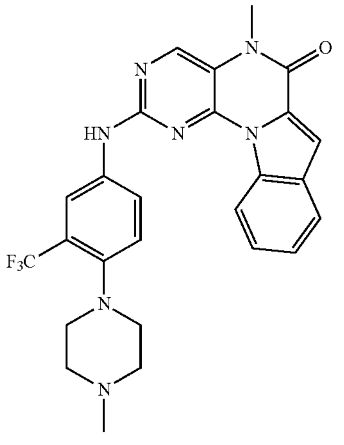
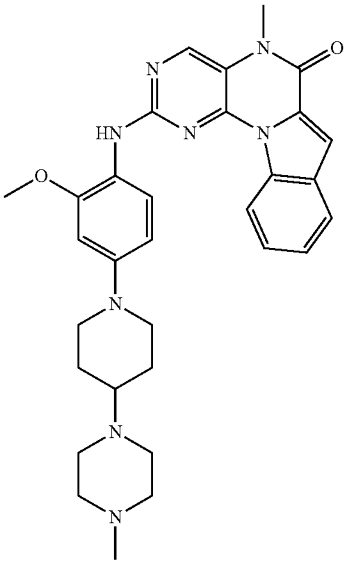

-continued
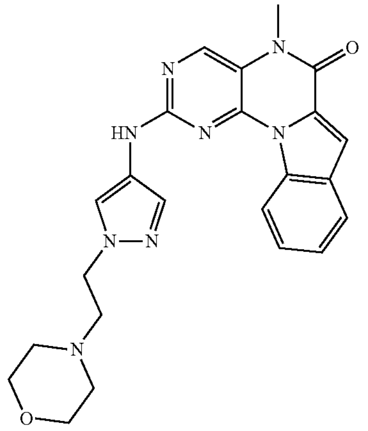
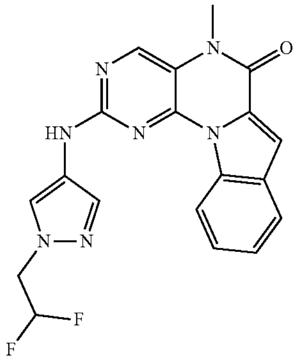
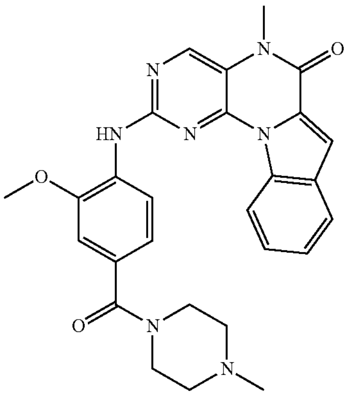
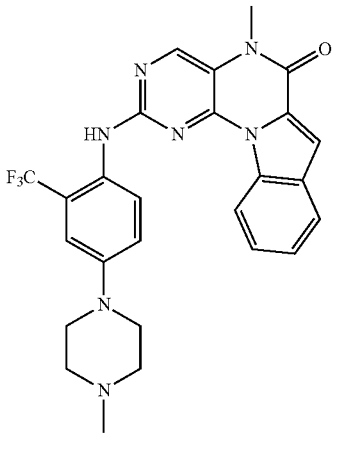
-continued
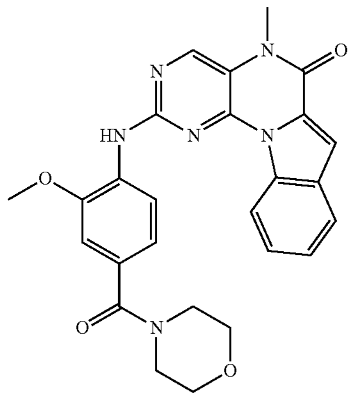
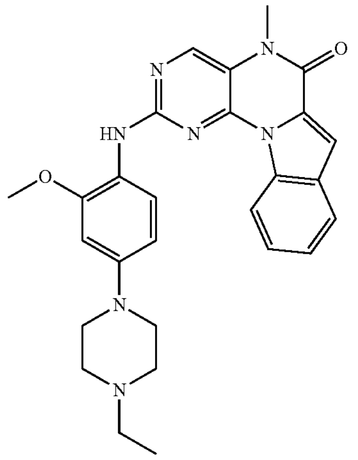
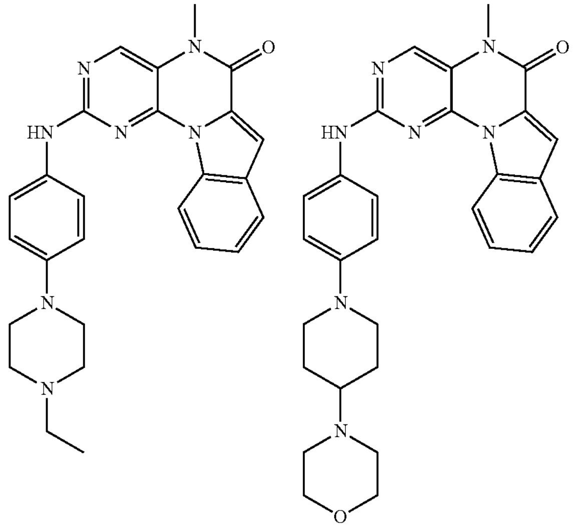

-continued
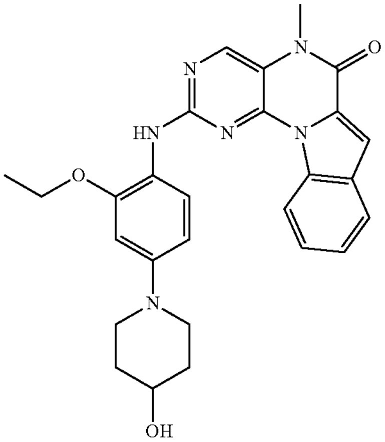
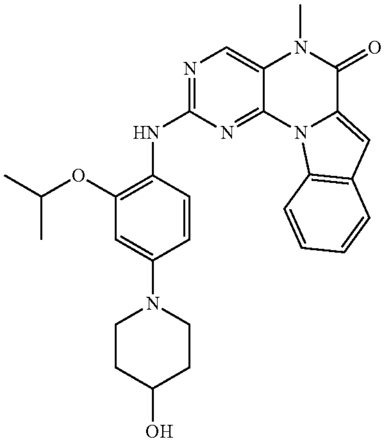
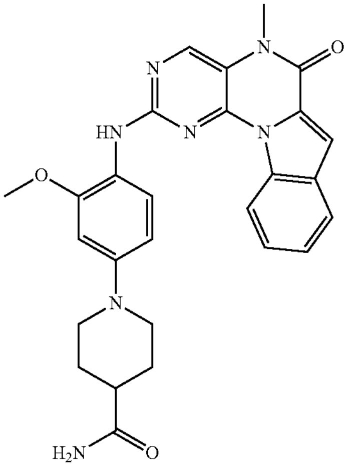
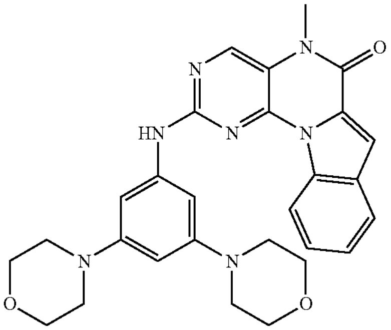
-continued
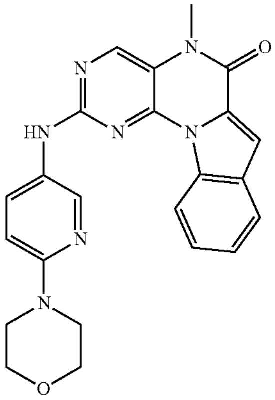
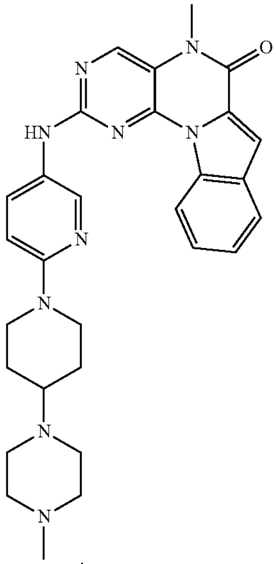
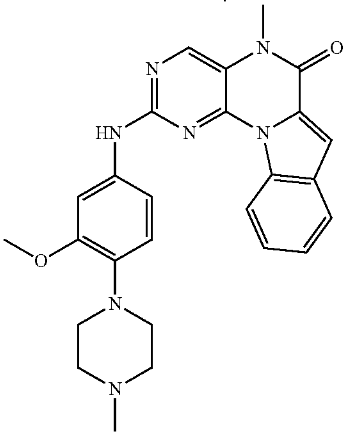
In an even more particular embodiment, the NEK6 inhibitor herein disclosed is a compound selected from the list consisting of ZINCO5007751, ZINC04384801, I-18, I-3 and I-1 with the respective structural formula:
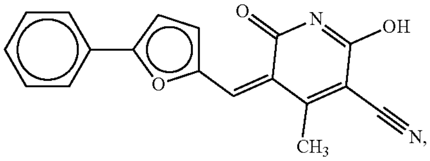
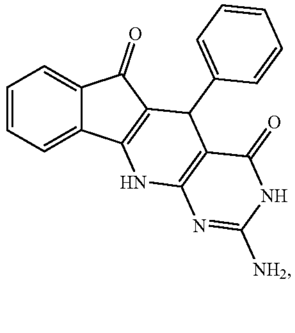

-continued

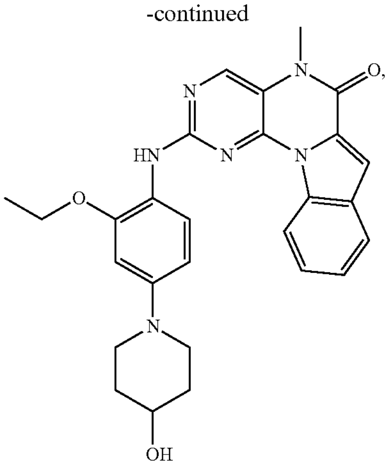

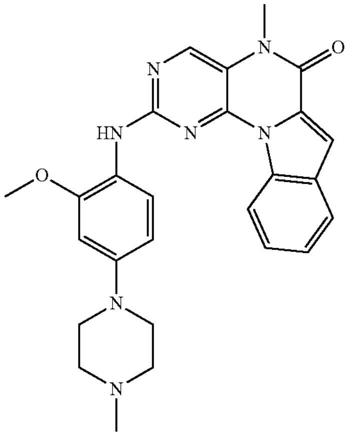

and

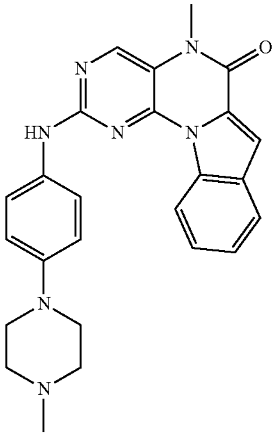

Other NEK6 inhibitors described in the art that are of use in the context of current invention, more particularly as part of a treatment of ALS and/or FTD, are staurosporine (CAS nr 62996-74-1), quercetine (CAS nr 117-39-5), epicocconigrone A with formula

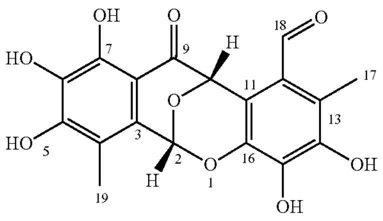 [SMILES: Cc1c(O)c(O)c2c(c1C=O)[C@@H]1O[C@H](O2)c2c(C)c(O)c(O)c(O)c2C1=O]

and molecular formula $C_{18}H_{14}O_9$ (El Amrani et al 2014 J Nat Prod 77, 49-56), or the closely related analogue epicoccolide A. Epicocconigrone A and epicoccolide A differ only in the D ring, in which the positions of Me-19 and 7-OH of the former are opposite of those of the latter.

In other embodiments, the NEK6 inhibitor of current invention is

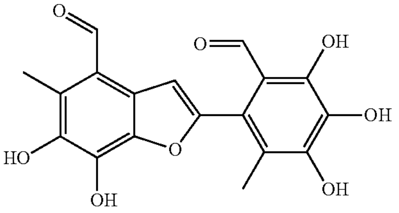 [SMILES: Cc1c(O)c(O)c(O)c(C=O)c1-c1cc2c(C=O)c(C)c(O)c(O)c2o1]

as described in El Amrani et al (2014 J Nat Prod 77, 49-56), or

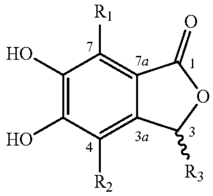

wherein R1 is OH, R2 is CH3 and R3 is H (El Amrani et al 2014 J Nat Prod 77, 49-56), or

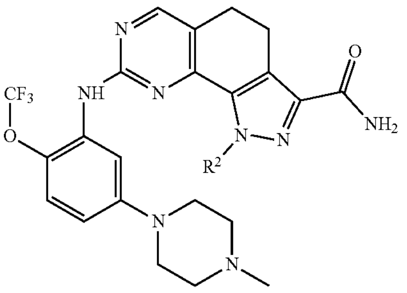

wherein $R^2$ is methyl, 2-fluoro-ethyl or vinyl (Beria et al 2010 Bioorg Med Chem Lett 20, 6489-6494), or

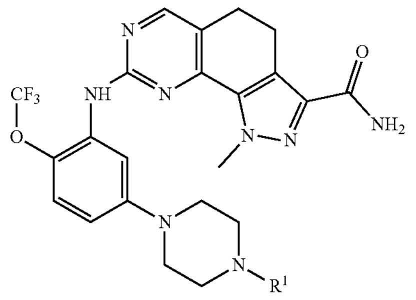

wherein $R^1$ is H (Beria et al 2010 Bioorg Med Chem Lett 20, 6489-6494), or 5-epi-nakijiquinone N with formula:

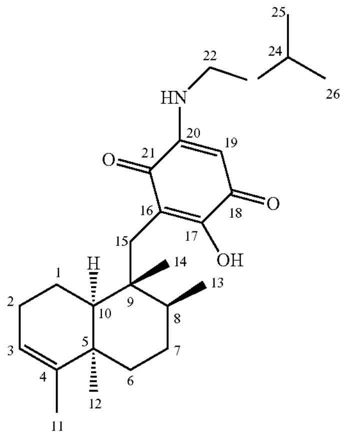

and with molecular formula $C_{26}H_{39}NO_3$ (Daletos et al 2014 J Nat Prod 77, 218-226), or 5-epi-nakijinol C with formula:

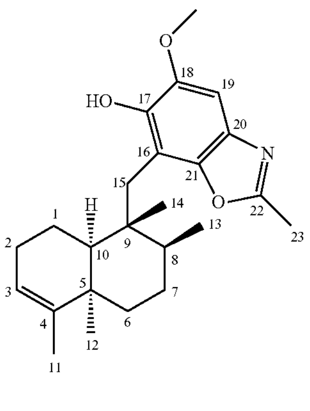 [SMILES: COc1cc2nc(C)oc2c(C[C@]2(C)[C@@H](C)CC[C@@]3(C)C(C)=CCC[C@@H]23)c1O]

and molecular formula $C_{24}H_{33}NO_3$ (Daletos et al 2014 J Nat Prod 77, 218-226), or 18-hydroxy-5-epihyrtiophenol with formula:

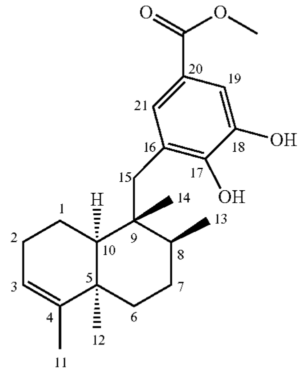 [SMILES: COC(=O)c1cc(O)c(O)c(C[C@]2(C)[C@@H](C)CC[C@@]3(C)C(C)=CCC[C@@H]23)c1]

as described in Salmoun et al (2000 J Nat Prod 63, 452-456) and Daletos et al (2014 J Nat Prod 77, 218-226), or anomalin A with formula:

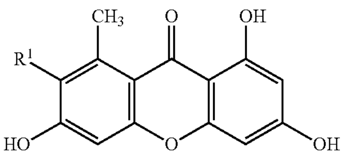

wherein $R^1$ is OH (Ebada et al 2011 Bioorg Med Chem 19, 4644-4651).

NEK6 Kinase Assay

The functionality of the NEK6 inhibitors disclosed above can be easily tested by the skilled person using well-known methods in the art without any experimental burden. A non-limiting example of such an assay is the NEK6 kinase assay as described in De Donato et al (2018). Activity of potential NEK6 inhibitors can be tested using the LANCE NEK6 Ultra Kinase Assays protocol (U-TRF #25 technical note, PerkinElmer, Monza, MB). Compounds are first tested at 30 μM and incubated with 4 nM NEK6 (Carna, Chuo-ku, Kobe, Japan, #05-130), 50 nM ULight-p70 S6K Peptide (PerkinElmer #TRF0126) and 100 μM ATP (Sigma-Aldrich, Saint Louis, U.S.A, #A2383) at room temperature. NEK6 has been shown to phosphorylate and activate p70 S6 kinase in vitro (Belham et al 2001 Curr Biol 11:1155-1167). Kinase reactions are terminated after 90 minutes by the addition of EDTA and the signal is e.g. read with the Enspire plate reader (PerkinElmer) in TR-FRET mode (excitation at 320 nm and emission at 665 nm) after 60 minutes. Inhibition of NEK6 activity can be calculated as percentage with respect to the control sample (100% of activity). Quercetin can be used as positive control (Molport). For IC50 determinations, the compounds can be tested at various dilutions and the dose inhibiting 50% of NEK6 activity (IC50) can be calculated using the GraphPad Prism 5.0 Software (San Diego, CA, USA).

Other NEK6 kinase assay kits are commercially available e.g. from BPSBioscience based on Yin et al (2003 J Biol Chem 278:52454-52460).

Detection of NEK6 Inhibition

The effectivity of NEK6 inhibitors herein disclosed in inhibiting NEK6 expression in cells both in vitro or in vivo can also be tested by various well-known techniques. For example, inhibition of NEK6 expression induced by e.g. oligonucleotide inhibitors or nuclease-based inhibitors can be determined by measuring levels of the NEK6 mRNA or the NEK6 protein in the cells, using standard techniques for isolating and quantifying mRNA or protein (e.g. by RT-PCT, Western blot analysis using commercially available anti-NEK6 antibodies).

Administration

NEK6 gene inactivation, i.e. inhibition of functional expression of the target gene, can be achieved through the creation of transgenic organisms expressing one of the oligonucleotide or nuclease-based inhibitor (e.g. antisense RNA), or by administering said inhibitor to the subject (see Example 1-2 of the application). The nature of the inhibitor and whether the effect is achieved by incorporating the nucleotide inhibitor into the subject's genome or by administering the inhibitor is not vital to the invention, as long as said inhibitor inhibits the functional expression of the NEK6 gene. An antisense construct can be delivered, for example, as an expression plasmid, which, when transcribed in the cell, produces an oligonucleotide that is complementary to at least a unique portion of the cellular NEK6 RNA. Alternatively, oligonucleotide inhibitors such as siRNA can also be expressed from recombinant circular or linear DNA plasmids using any suitable promoter. Suitable promoters for expressing these inhibitors targeted against NEK6 from a plasmid include, for example, the U6 or H1 RNA pol III promoter sequences and the cytomegalovirus promoter. Selection of other suitable promoters is within the skill in the art. Non-limiting examples are neuronal-specific promoters, glial cell specific promoters, the human synapsin 1 gene promoter, the Hb9 promotor or the promoters disclosed in U.S. Pat. No. 7,341,847B2.

The recombinant plasmids of the invention can also comprise inducible or regulatable promoters for expression of the oligonucleotide inhibitor in a particular tissue or in a particular intracellular environment. The oligonucleotide inhibitor expressed from recombinant plasmids can either be isolated from cultured cell expression systems by standard techniques, or can be expressed intracellularly, e.g. in brain tissue or in neurons. Oligonucleotide inhibitors can also be expressed intracellularly from recombinant viral vectors. The recombinant viral vectors comprise sequences encoding the oligonucleotide inhibitors of the invention and any suitable promoter for expressing the oligonucleotide sequences. The oligonucleotides will be administered in an "effective amount" which is an amount sufficient to cause RNAi mediated degradation of the target mRNA, or an amount sufficient to inhibit the NEK6 activity. One skilled in the art can readily determine an effective amount of the inhibitor of the invention to be administered to a given subject, by taking into account factors such as axonal transport defects, axonal branching, the extent of the disease penetration, the age, health and sex of the subject, the route of administration and whether the administration is regional or systemic. Generally, an effective amount of inhibitor targeting NEK6 expression and/or activity comprises an intracellular concentration of from about 1 nanomolar (nM) to about 100 nM, preferably from about 2 nM to about 50 nM, more preferably from about 2.5 nM to about 10 nM. It is contemplated that greater or lesser amounts of inhibitor can be administered.

Drug Administration Across the Blood-Brain Barrier

The blood-brain barrier (BBB) is a protective layer of tightly joined cells that lines the blood vessels of the brain which prevents entry of harmful substances (e.g. toxins, infectious agents) and restricts entry of (non-lipid) soluble molecules that are not recognized by specific transport carriers into the brain. This poses a challenge in the delivery of drugs, such as the NEK6 inhibitors described herein, to the central nervous system/brain in that drugs transported by the blood not necessarily will pass the blood-brain barrier. Several options are nowadays available for delivery of drugs across the BBB (Peschillo et al. 2016, J Neurointervent Surg 8:1078-1082; Miller & O'Callaghan 2017, Metabolism 69:S3-S7; Drapeau & Fortin 2015, Current Cancer Drug Targets 15:752-768).

Drugs can be directly injected into the brain (invasive strategy) or can be directed into the brain after BBB disruption with a pharmacological agent (pharmacologic strategy). Invasive means of BBB disruption are associated with the risk of hemorrhage, infection or damage to diseased and normal brain tissue from the needle or catheter. Direct drug deposition may be improved by the technique of convection-enhanced delivery. Longer term delivery of a therapeutic protein can be achieved by implantation of genetically modified stem cells, by recombinant viral vectors, by means of osmotic pumps, or by means of incorporating the therapeutic drug in a polymer (slow release; can be implanted locally).

Pharmacologic BBB disruption has the drawback of being non-selective and can be associated with unwanted effects on blood pressure and the body's fluid balance. This is circumvented by targeted or selective administration of the pharmacologic BBB disrupting agent. As an example, intra-arterial cerebral infusion of an antibody (bevacizumab) in a brain tumor was demonstrated after osmotic disruption of the BBB with mannitol (Boockvar et al. 2011, J Neurosurg 114:624-632); other agents capable of disrupting the BBB pharmacologically include bradykinin and leukotriene $C_4$ (e.g. via intracarotid infusion; Nakano et al. 1996, Cancer Res 56:4027-4031).

BBB transcytosis and efflux inhibition are other strategies to increase brain uptake of drugs supplied via the blood. Using transferrin or transferrin-receptor antibodies as carrier of a drug is one example of exploiting a natural BBB transcytosis process (Friden et al. 1996, J Pharmacol Exp Ther 278:1491-1498). Exploiting BBB transcytosis for drug delivery is also known as the molecular Trojan horse strategy. Another mechanism underlying BBB, efflux pumps or ATP-binding cassette (ABC) transporters (such as breast cancer resistance protein (BCRP/ABCG2) and P-glycoprotein (Pgp/MDR1/ABCB1)), can be blocked in order to increase uptake of compounds (e.g. Carcaboso et al. 2010, Cancer Res 70:4499-4508). Therapeutic drugs can alternatively be loaded in liposomes to enhance their crossing of the BBB, an approach also known as liposomal Trojan horse strategy.

A more recent and promising avenue for delivering therapeutic drugs to the brain consists of (transient) BBB disruption by means of ultrasound, more particularly focused ultrasound (FUS; Miller et al. 2017, Metabolism 69:S3-S7). Besides being non-invasive, this technique has, often in combination with real-time imaging, the advantage of precise targeting to a diseased area of the brain. Therapeutic drugs can be delivered in e.g. microbubbles e.g. stabilized by an albumin or other protein, a lipid, or a polymer. Therapeutic drugs can alternatively, or in conjunction with microbubbles, be delivered by any other method, and subsequently FUS can enhance local uptake of any compound present in the blood (e.g. Nance et al. 2014, J Control Release 189:123-132). Just one example is that of FUS-assisted delivery of antibodies directed against toxic amyloid-beta peptide with demonstration of reduced pathology in mice (Jordao et al. 2010, PloS One 5:e10549). Microbubbles with a therapeutic drug load can also be induced to burst (hyperthermic effect) in the vicinity of the target cells by means of FUS, and when driven by e.g. a heat shock protein gene promoter, localized temporary expression of a therapeutic protein can be induced by ultrasound hyperthermia (e.g. Lee Titsworth et al. 2014, Anticancer Res 34:565-574). Alternatives for ultrasound to induce the hyperthermia effect are microwaves, laser-induced interstitial thermotherapy, and magnetic nanoparticles (e.g. Lee Titsworth et al. 2014, Anticancer Res 34:565-574).

Intracellular Drug Administration

Besides the need to cross the BBB, drugs targeting disorders of the central nervous system, such as the NEK6 inhibitors described herein, may also need to cross the cellular barrier. One solution to this problem is the use of cell-penetrating proteins or peptides (CPPs). Such peptides enable translocation of the drug of interest coupled to them across the plasma membrane. CPPs are alternatively termed Protein Transduction Domains (TPDs), usually comprise 30 or less (e.g. 5 to 30, or 5 to 20) amino acids, and usually are rich in basic residues, and are derived from naturally occurring CPPs (usually longer than 20 amino acids), or are the result of modelling or design. A non-limiting selection of CPPs includes the TAT peptide (derived from HIV-1 Tat protein), penetratin (derived from *Drosophila* Antennapedia—Antp), pVEC (derived from murine vascular endothelial cadherin), signal-sequence based peptides or membrane translocating sequences, model amphipathic peptide (MAP), transportan, MPG, polyarginines; more information on these peptides can be found in Torchilin 2008 (Adv Drug Deliv Rev 60:548-558) and references cited therein.

CPPs can be coupled to carriers such as nanoparticles, liposomes, micelles, or generally any hydrophobic particle. Coupling can be by absorption or chemical bonding, such as via a spacer between the CPP and the carrier. To increase target specificity an antibody binding to a target-specific antigen can further be coupled to the carrier (Torchilin 2008, Adv Drug Deliv Rev 60:548-558). CPPs have already been used to deliver payloads as diverse as plasmid DNA, oligonucleotides, siRNA, peptide nucleic acids (PNA), proteins and peptides, small molecules and nanoparticles inside the cell (Stalmans et al. 2013, PloS One 8:e71752).

Diseases

Current invention provides methods to treat dipeptide repeat toxicity and neurological diseases caused thereby. Particular diseases that are subject to this invention are ALS, FTD and ALS with FTD. ALS is a neurodegenerative disease with loss of upper (located in the brain) and lower (located in the spinal cord) motor neurons that leads to paralysis, dysphagia, dysarthria and eventually respiratory failure. FTD or frontotemporal degeneration is a progressive brain disease with changes in behaviour, personality, and language dysfunction due to loss of nerve cells in the frontal and temporal lobes. Both FTD and ALS are heterogeneous at the clinical, neuropathological and genetic levels and, even though they come across as distinct progressive disorders, there is increasing evidence of the fact that they share some clinical, neuropathological and genetic features. This implies that these two disorders: a) share neurodegenerative pathways and b) may be part of a common spectrum. Indeed, as many as half of the people diagnosed with ALS exhibit behavioural changes or a decline in language skills similar to those observed in FTD. Conversely, up to 30% of people diagnosed with FTD develop motor symptoms consistent with ALS.

It is now recognized that the C9orf72 gene is the most common gene causing hereditary FTD, ALS and ALS with FTD. The C9orf72 gene mutation produces an expansion of an area of the gene consisting of six nucleotides, called a hexanucleotide repeat of GGGGCC. Carriers of this gene expansion can have hundreds to thousands of repeats of the hexanucleotide compared to only a few in someone without C9orf72-related ALS or FTD. A small number of other genes have also been shown to have a role in inherited ALS with frontotemporal degeneration. These are VCP, SQSTMI, UBQLN2 and CHMP2B.

In a most particular embodiment, the method of treatments herein disclosed are envisaged to treat ALS and/or FTD patients carrying the C9orf72 mutation, more specifically phrased carrying the $G4C_2$ repeat expansion mutation in C9orf72.

In particular embodiments, the application provides the inhibitors herein disclosed for use as a medicament. In further particular embodiments, the inhibitors herein disclosed are provided for use to treat axonal transport defects or to reduce axonal transport defects in a subject's neurons. "To reduce" as used herein refers to a statistically significant reduction of axonal transport defects in the presence of the inhibitor of the description compared to the absence of the inhibitor.

In another particular embodiment, the inhibitors herein disclosed are provided for use to treat dipeptide repeat toxicity, more particularly to treat axonal transport defects in a subject suffering from dipeptide repeat toxicity. In even more particular embodiments, the inhibitors herein disclosed are provided for use in the treatment of ALS, FTD and/or ALS with FTD. In a most particular embodiment, the inhibitors herein disclosed are provided for use to treat C9orf72-mediated ALS and/or FTD or to treat subjects suffering from ALS and/or FTD and/or carrying the C9orf72 mutation and/or carrying C9orf72 repeat expansions, more particularly $G4C_2$ repeat expansions.

Nek6 as Biomarker

As demonstrated in Example 5, a significant upregulation of both NEK1 and NEK6 mRNA expression was observed in blood samples from ALS patients carrying C9orf72 repeat expansions compared to healthy controls and sporadic ALS patients. Therefore, in another aspect, the invention provides NEK1 and/or NEK6 for use as a biomarker for C9FTD/ALS, more particularly for ALS and/or FTD caused by C9orf72 repeat expansions.

Or alternatively phrased, a method of diagnosing a patient with C9FTD/ALS, more particularly ALS and/or FTD caused by the C9orf72 mutation is provided, comprising the steps of:

- Determining the expression level of NEK1 and/or NEK6 in a sample obtained from the patient;
- Comparing said expression level with that from a control sample obtained from a healthy subject or determining that the expression level of NEK6 and/or NEK1 is statistically significantly increased as compared to a healthy subject;
- Diagnosing the patient with C9FTD/ALS, more particularly with C9orf72-ALS and/or C9orf72-FTD when the NEK1 and/or NEK6 expression in the sample of the patient is statistically significantly higher than that in the control sample.

In one embodiment, said sample is a blood, serum or plasma sample. In a most particular embodiment, said sample is a peripheral blood mononuclear cell sample.

NEK1 as used herein refers to the human serine/threonine protein kinase NEK1 as depicted in SEQ ID No. 3.

The invention also provides a method of diagnosing and treating C9FTD/ALS, more particularly C9orf72-ALS and/or C9orf72-FTD in a patient, comprising the steps of:

Determining the expression level of NEK1 and/or NEK6 in a sample obtained by the patient;

Comparing said expression level with that from a control sample obtained from a healthy subject or determining that the expression level of NEK6 and/or NEK1 is statistically significantly increased as compared to a healthy subject;

Applying an ALS treatment to the patient when the detected expression level of NEK1 and/or NEK6 is statistically significantly higher than that of the control sample.

In one embodiment, said ALS treatment comprises administration to the subject of a medicament selected from the list consisting of RADICAVA® (or EDARAVONE™) RILUTEK® (or RILUZOLE™), TIGLUTIK®, NUEDEXTA® and a sodium phenylbutyrate-taurursodiol formulation.

A "control sample" as used herein refers to a sample derived from a healthy subject not comprising C9orf72 repeat expansions, more particularly $G4C_2$ repeat expansions.

SNRK Inhibition as Treatment of Axon Transport Defects

Besides the methods of the invention disclosed above comprising administering a NEK6 inhibitor to a subject, the invention also provides a SNRK inhibitor for use in the treatment of axonal transport defects, especially in ALS or FTD patients or in ALS patients with FTD. Therefore, in a further aspect, a SNRK inhibitor is provided for use as a medicament. In one embodiment, the SNRK inhibitor is provided for use to reduce axonal transport defects in a subject's neurons. Particularly, for use in a treatment of a disease related to dipeptide repeat toxicity, more particularly to ALS, FTD or ALS with FTD, even more particularly to ALS and/or FTD caused by a C9orf72 repeat expansion mutation. Alternatively phrased, the invention provides a method to reduce axonal transport defects in a subject's neurons comprising the step of administering a SNRK inhibitor to said subject. Particularly, to treat a disease related to dipeptide repeat toxicity, more particularly to ALS, FTD or ALS with FTD, even more particularly to ALS and/or FTD caused by a C9orf72 repeat expansion mutation.

SNRK is a member of the sucrose nonfermenting (SNF)-related kinase family of serine/threonine kinases (Kertesz et al 2002 Gene 294:13-24). It is also known as SNF Related Kinase, SNF-Related Serine/Threonine-Protein Kinase, SNF1-Related Kinase, EC 2.7.11.1, KIAA0096, HSNFRK, SNF-1 Related Kinase, EC 2.7.11, FLJ20224 and SNFRK. In a most particular embodiment, SNRK as used herein refers to human SNRK as depicted in SEQ ID No. 2.

In a particular embodiment, the SNRK inhibitor provided herein reduces the expression of SNRK. In a particular embodiment, the SNKR inhibitor is an oligonucleotide, more particularly an RNA silencing agent, even more particularly, an RNA silencing agent selected from the list consisting of a siRNA, shRNA, dsRNA, divalent siRNA (di-siRNA), antisense oligonucleotides (ASO), gapmer, microRNA, ribozyme, DNAzyme, nucleic acid aptamer, locked nucleic acid (LNA), bridged nucleic acid (BNA), ethyl bridged nucleic acid (ENA), peptide nucleic acid (PNA) and morpholino oligonucleotide.

In another embodiment, the SNRK inhibitor comprises a nuclease. In a particular embodiment, the SNRK inhibitor is a CRISPR-Cas, a TALEN, a meganuclease or a Zinc-finger nuclease.

EXAMPLES

Figure 2:
FIG. 2 shows a Western blot detecting Cas9 expression in DIV80 PSC-neuronal progeny before (Wo Dox) and after (+Dox) doxycycline mediated expression.

Example 1. a Kinome-Wide CRISPR Knock-Out (KO) Screen in Human iPSC-Derived Cortical Neurons In order to find inhibitors of DPR toxicity, the inventors of current application initiated a pooled CRISPR knock-out screen. As kinase activation is crucial for neuronal survival, and kinases are druggable targets, the inventors set off to find kinase inhibitors to treat DPR toxicity. First, several inducible Cas9 (iCas9) expressing human induced pluripotent stem cell (hiPSC) lines were established by inserting a single copy of the coding region of Cas9 into the AAVS1 locus under control of a TET-On promoter system (Ordovas et al 2015 Stem Cell Reports 5:918-931). As Cas9 expression is doxycycline dependent, this enables induction of its expression at any stage during iPSC differentiation, here specifically in DIV70-85 iPSC-derived cortical neurons. Because most sgRNA lentiviral libraries used for large screens contain a puromycin selectable cassette, a neomycin antibiotic resistance cassette was used to select for cells containing the iCas9 construct. The correct insertion of the Cas9 cassette was confirmed by a combination of 3' and 5' junction assay PCR and digital droplet PCR. Induction of Cas9 expression was confirmed by Western blot and immunostaining in iPSCs. To proof the functionality of Cas9, iPSCs were transduced with individual sgRNAs, and a T7EI analysis was used to demonstrate cleavage of the target genes following induction of Cas9 (data not shown). Finally, cell identity, pluripotency, and genome integrity were confirmed by single nucleotide polymorphism (SNP) PCR, embryoid body analysis, and array comparative genome hybridization (data not shown). It is demonstrated, using a protocol adapted from Shi et al. (2012 Nat Protoc 7: 1836-1846)), that these iPSC lines could be differentiated into ±90% TUJ1 positive neurons on DIV70-85, containing a mixture of cells with layer VI and V cortical fate (FIG. 1). Following doxycycline administration, expression of Cas9 in cortical neurons was confirmed by qRT-PCR, Western blot and immunostaining (FIG. 2 and data not shown). Therefore, these iCas9 hiPSCs can be used for CRISPR/Cas9 screens in iPSC-derived cortical progeny.

Figure 3:
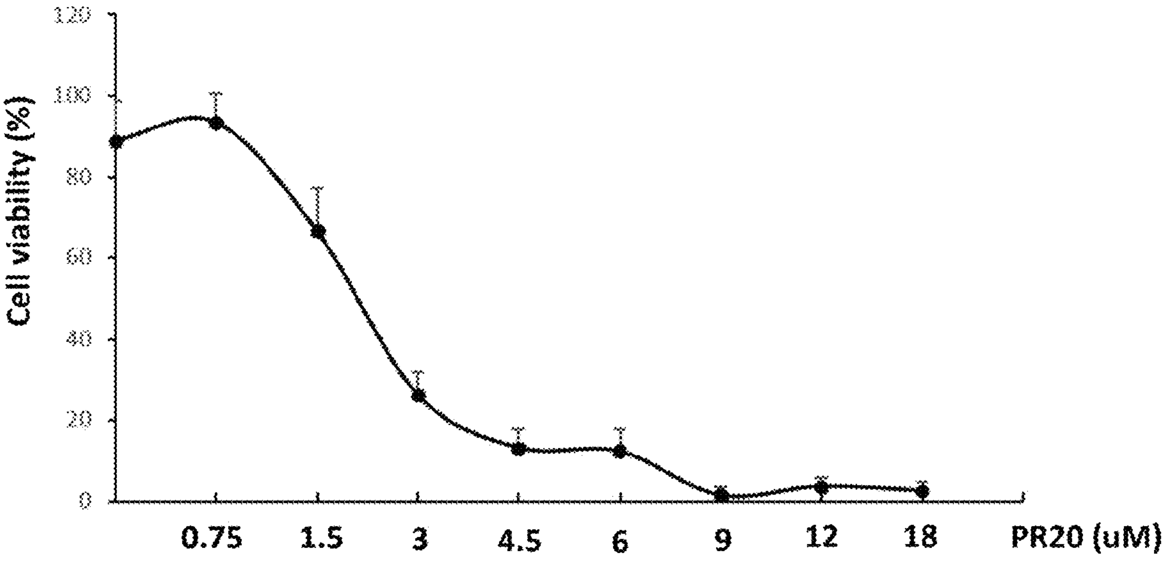
FIG. 3 is a dose response curve of the PR20 dose-dependent cytotoxicity on DIV80 PSC neuronal progeny measured by Cell Viability Assay after a 24 h treatment. Y-axis represents cell viability in %, X-axis represent the concentration of administered PR20 in μM.

Next, the iCas9-iPSC derived DIV79 neurons were treated with PR20 peptides to mimic DPR toxicity (Cheng et al 2019 Neuron 72:1-14; Kramer et al 2018 Nat Genet 50:603-612). Poly-PR (proline/arginine) was readily taken up and showed partial nuclear localization 24 h after treatment (data not shown). A dose-response curve demonstrated that ±70-80% iCas9-iPSC DIV80 neuronal progeny died when treated with 6 μM PR20 (FIG. 3).

Figure 4:
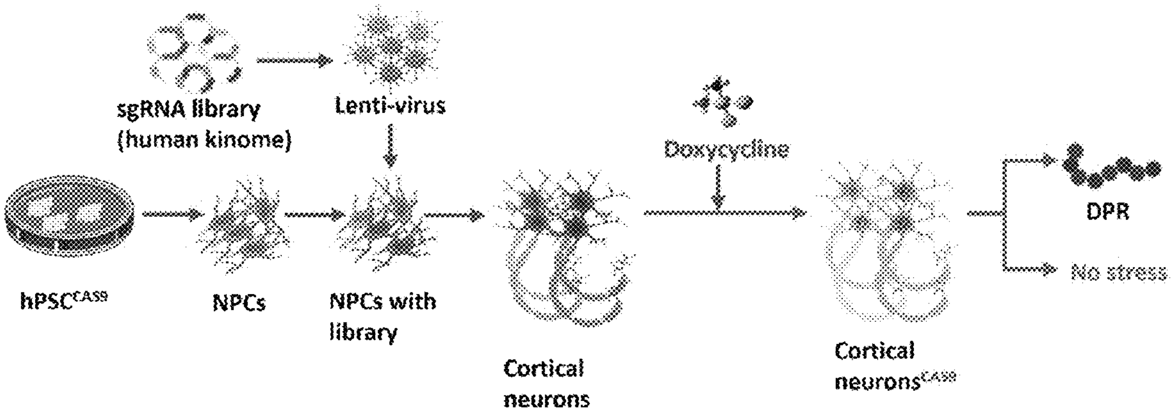
FIG. 4 is a schematic representation of the CRISPR/Cas screen procedure: DIV46 NPCs were transduced with the kinome-wide Brunello sgRNA vector library and transduced cells were selected with 1 μg/ml Puromycin; NPCs were differentiated to DIV70 cortical neurons, after which 3 μg doxycycline was added for 5 days to induce Cas9, followed by treatment of 50% of the DIV79 neuronal progeny with or without 6 mM PR20. The surviving cells were subjected to deep sequencing and statistical analysis for sgRNA distribution. 5 biological replicates were performed.

This PR20 concentration was then used for the CRISPR/Cas9 live-death screen, following transduction with the Brunello human kinome-wide CRISPR KO pooled sgRNA library. iCas9 hiPSCs were differentiated into neuroprogenitor cells (NPCs), and NPCs were transduced with the lentiviral kinome sgRNA library at a multiplicity of infection (MOI) of 0.3 (FIG. 4). Transduced cells were selected by puromycin. RNA sequencing performed on DIV80 cortical progeny from these transduced iCas9-NPCs demonstrated robust cortical neuronal differentiation (data not shown). sgRNA transduced NPCs were then differentiated to cortical neurons until DIV70, treated with doxycycline to induce Cas9 expression for 5 days, followed by PR20 treatment for 24 h (FIG. 4). Next Generation Sequencing (NGS) was performed to identify sgRNAs enriched or depleted in the surviving PR20 treated cells. The screen identified 243 candidate genetic modifiers of PR20 toxicity, including 113 genes that enhanced and 130 that suppressed survival. Gene ontology analysis performed on the 113 genes that, when targeted by the CRISPR/Cas9, protected cells from PR20-mediated toxicity, identified genes involved in axon regeneration, dendrite development, apoptosis, and cytoskeletal organization.

Example 2. NEK6 Downregulation Rescues DPR Toxicity

Figure 5:
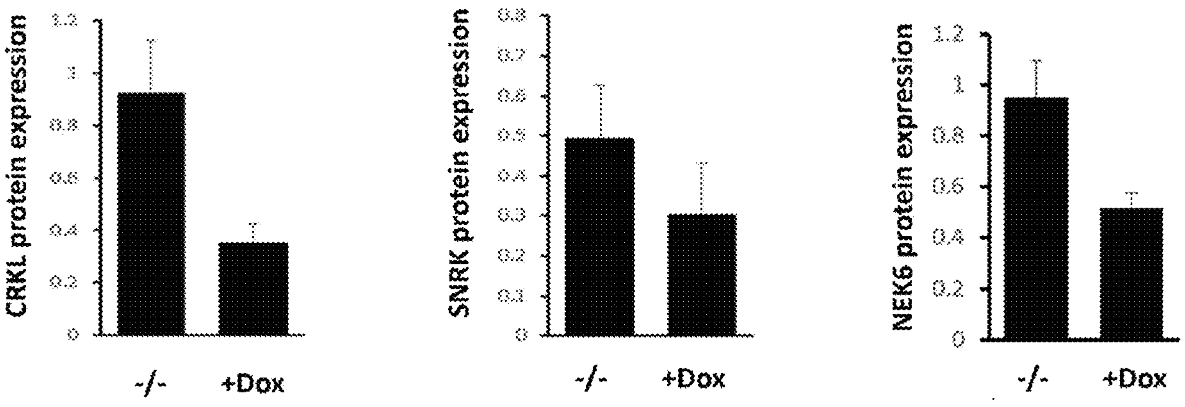
FIG. 5 shows the quantified protein levels detected in a Western blot of CRKL (left), SNRK (middle) and NEK6 (right) in DIV80 neurons following transduction with single sgRNAs against CRKL, SNRK or NEK6 respectively in the absence (−/−) and presence of doxycycline (+Dox). The data were normalized to α-Tubulin or GAPDH.
Figure 6:
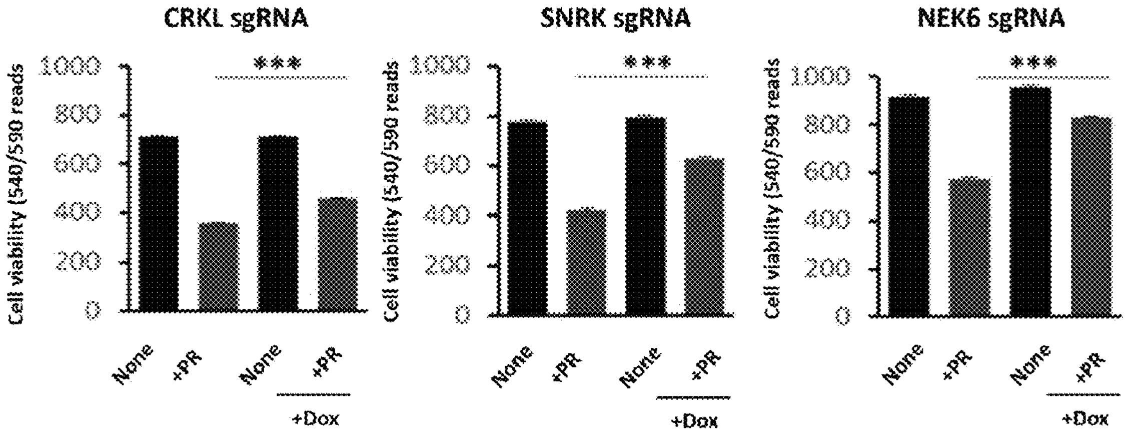
FIG. 6 shows the cell viability data of Cas9-hiPSC derived DIV47 neurons transduced with sgRNAs against CRKL (left), SNRK (middle) or NEK6 (right) with (+PR) and without (None) 6 μM PR20 treatment for 24 h (n>10) and in the absence and presence (+Dox) of doxycycline. One-way ANOVA with post-hoc Tukey's test, *** represents p-value of 0.001. Data values represent mean±SEM.

To validate results from the screen, iCas9-NPCs were individually transduced with sgRNAs directed against the top 3 candidate genes, CRKL, SNRK and NEK6, that enhanced survival in the interference screen. A 50-60% reduction in protein levels of CRKL, SNRK and NEK6 was observed after doxycycline treatment (FIG. 5). When cells were exposed to PR20 peptides, an increased survival was noted for cells transduced with sgRNAs against all three genes (FIG. 6). A more pronounced effect could be observed using sgRNAs against NEK6 and SNRK.

Figure 7:
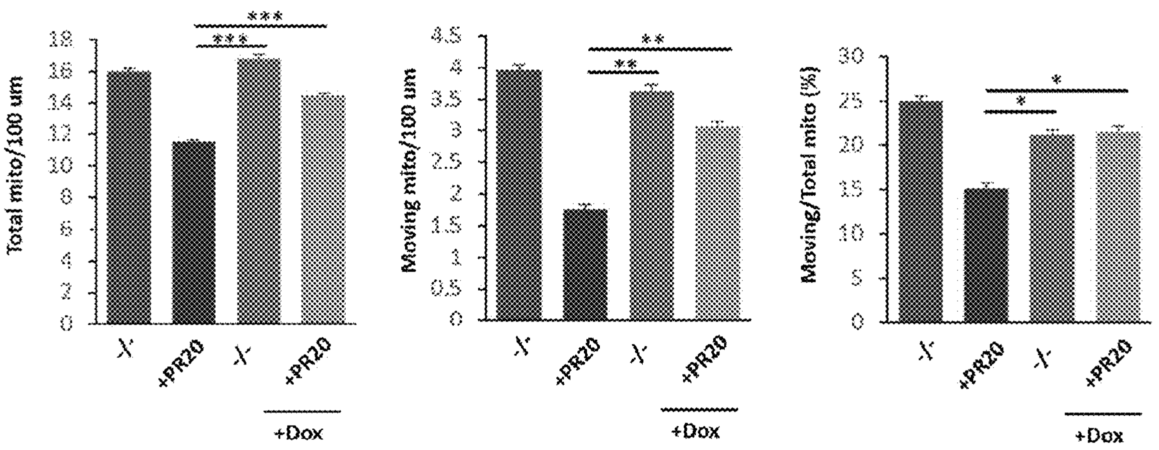
FIG. 7 shows the quantification of total mitochondria (left), moving mitochondria (middle) and the ratio of moving to total mitochondria (right) normalized to a neurite length of 100 m and during a time period of 200 s. Experiments were done in iCas9-hiPSC derived cortical neurons obtained from iCas9-iPSC derived cortical neurons transduced with NEK6 sgRNA loaded with Mito-Tracker-Red. −/−=no treatment; +PR20=PR20 treatment; +Dox=doxycycline treatment; +PR20+Dox=PR20 and doxycycline treatment. One-way ANOVA with post-hoc Tukey's test, *, , *, **** represent p-values of 0.05, 0.01, 0.001 and 0.0001, respectively. Data values represent mean±SEM.
Figure 8:
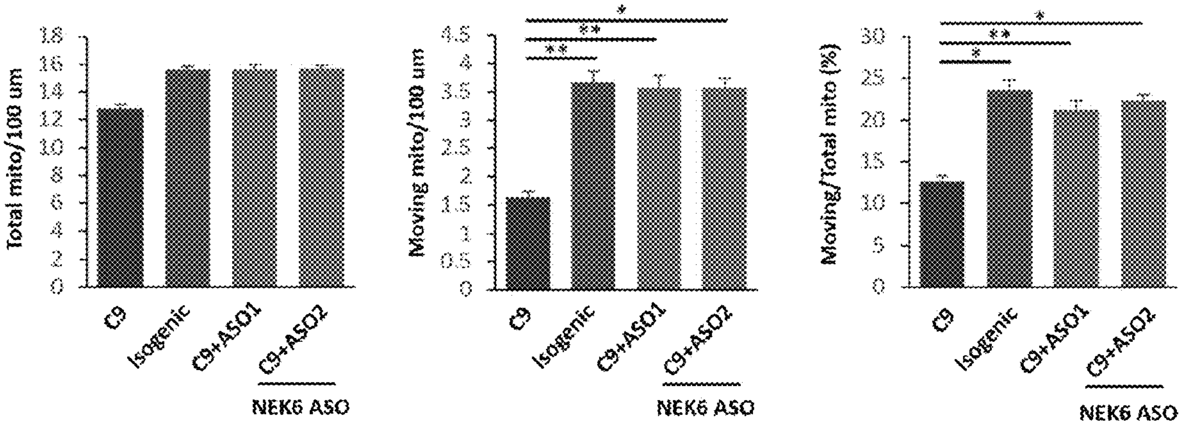
FIG. 8 shows the quantification of total mitochondria (left), moving mitochondria (middle) and the ratio of moving to total mitochondria (right) normalized to a neurite length of 100 m and during a time period of 200 s. Experiments were done in the respective hiPSC-derived cortical neurons from C9orf72 patient iPSC-derived and isogenic control iPSC-derived neurons, both treated with or without different NEK6 ASOs for 1 week. One-way ANOVA with post-hoc Tukey's test, *, ** represent p-values of 0.05, 0.01, respectively. Data values represent mean±SEM.

Axonal transport defects are an early event in the pathogenesis of ALS (Guo et al 2019 Semin Cell Dev Biol 99:133-150). To assess whether axonal transport defects also occur in cortical neurons from healthy donor hiPSC-cortical neurons treated with PR20 and from C9orf72 patient-derived cortical neurons, mitochondrial transport studies were performed. Consistent with our recent study (Fumagalli et al 2019 bioRxiv doi:10.1101/835082), treatment of normal donor iPSC-DIV79 cortical neurons with 1.5 μM PR20 significantly decreased axonal transport (FIG. 7). Axonal transport was also decreased in C9orf72 patient-derived hiPSC cortical neurons, but not in their isogenic controls (FIG. 8). This demonstrates that axonal transport is also defective in cortical neurons. To assess whether sgRNA-mediated knockdown of NEK6 would reverse axonal transport defects caused by poly(PR), we transduced healthy donor iCas9-hiPSC NPCs with a NEK6 sgRNA, treated DIV70 neural progeny with doxycycline and afterwards with a non-lethal dose of PR20 (1.5 μM). Knockdown of NEK6 resulted in a clear rescue of axonal transport defects caused by PR20 treatment (FIG. 7).

Figure 9:
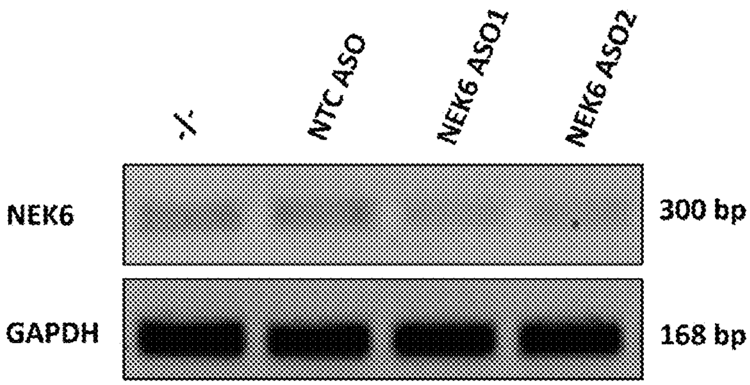
FIG. 9 shows RT-PCR validation of ASO-mediated knockdown of NEK6 in hiPSC derived cortical neurons and shows that a 100% reduction of NEK6 expression is not needed. Two different NEK6 ASOs and one scrambled ASO were used.

To test if a similar rescue of axonal transport could be demonstrated in cortical neurons from C9orf72 patient iPSCs, we treated DIV72 C9orf72-iPSC neural progeny with antisense oligonucleotides (ASOs) targeting NEK6. RT-PCR demonstrated a clear decrease in NEK6 transcripts in ASO-treated neurons (FIG. 9). Similar to what is observed for PR20-treated normal donor neuronal progeny in which NEK6 expression was reduced (FIG. 7), a significant rescue of axonal transport was observed in C9orf72 iPSC-cortical neurons treated with multiple anti-NEK6 ASOs (FIG. 8).

Example 3. NEK6 Rescues DPR Toxicity In Vivo

Figure 10A:
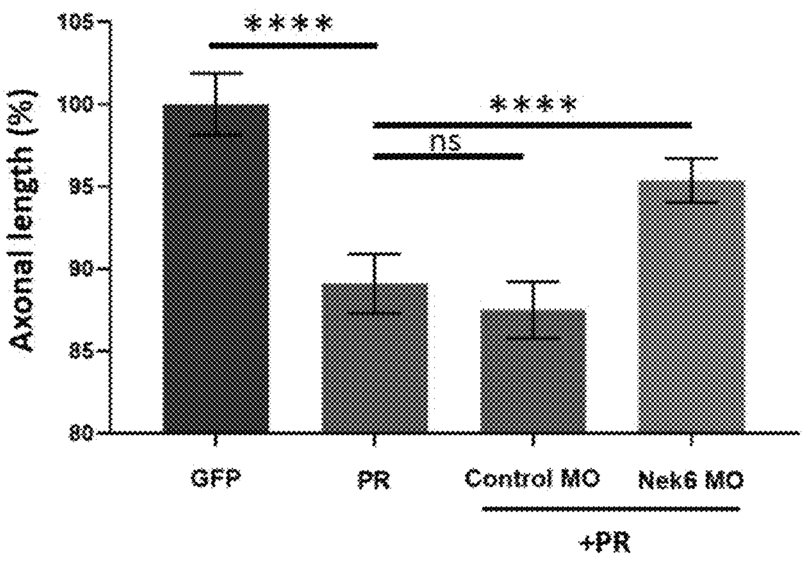
FIG. 10A and FIG. 10B shows quantification of (FIG. 10A) axonal length (data represent mean±95% CI; One-way ANOVA) and (FIG. 10B) aberrant axonal branching (data represent mean±95% CI; logistic regression) of zebrafish embryos injected with 0.844 μM GFP mRNA (GFP), 0.844 μM poly(PR) mRNA (PR), 0.844 μM poly(PR) mRNA plus 0.5 mM control morpholino (Control MO+PR) or 0.844 μM poly(PR) mRNA plus 0.5 mM Nek6 morpholino (Nek6 MO+PR); n=4 biological replicates. One-way ANOVA with post-hoc Tukey's test, *, *** represent p-values of 0.05, 0.001 respectively. Data values represent mean±SEM.
Figure 10B:
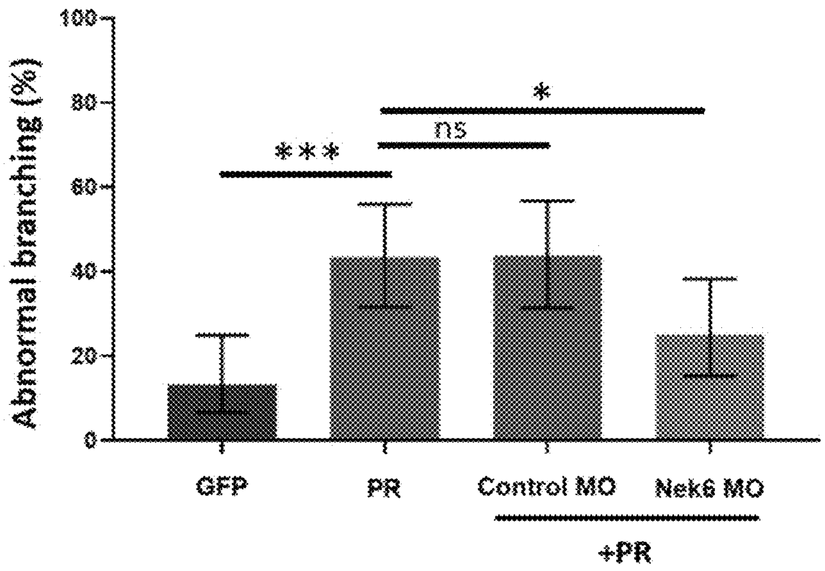

Next, the inventors sought to confirm the in vitro data in an in vivo model. Therefore, a morpholino-mediated NEK6 knockdown was performed in a poly(PR) zebrafish model as described in Swinnen et al (2018 Acta Neuropathol doi: 10.1007/s00401-017-1796-5). In this model, micro-injection of poly(PR) encoding mRNA results in a motor axonopathy in zebrafish embryos, characterised by reduced axonal lengths and aberrant axonal branching (Swinnen et al 2018 Acta Neuropathol doi:10.1007/s00401-017-1796-5). Co-injection in zebrafish oocytes of poly(PR) mRNA with a splice-blocking morpholino, specifically targeting the exon5-intron5 splice junction of the zebrafish NEK6 orthologue (i.e. nek6), significantly prevented the poly(PR)-induced axonal phenotype. More specifically, we observed a partial normalization of the axonal length (FIG. 10A) and noted less aberrantly branched axons (FIG. 10B).

Example 4. Chemical NEK6 Inhibition Rescues DPR Toxicity

Figure 11:
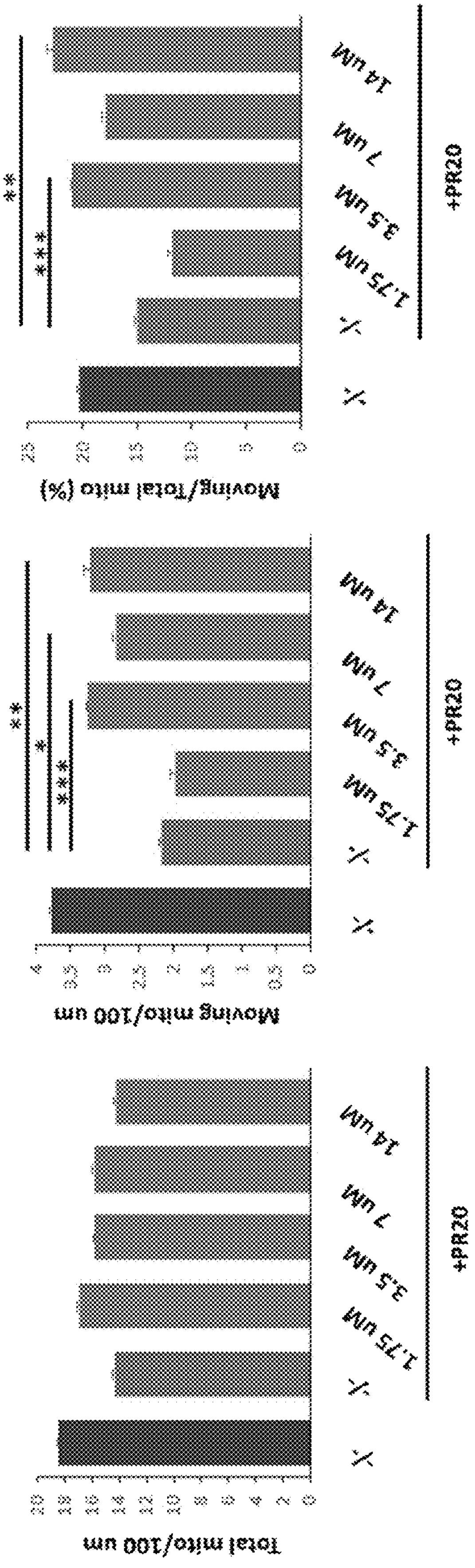
FIG. 11 shows the quantification of total mitochondria (left), moving mitochondria (middle) and ratio of moving to total mitochondria (right) normalized to a neurite length of 100 m in hiPSC-derived cortical neurons treated with PR20 peptides (+PR20) and different concentrations of the NEK6 inhibitor (0, 1.75, 3.5, 7, 14 μM) which were added 3 days before PR20 treatment. One-way ANOVA with post-hoc Tukey's test, *, , * represent p-values of 0.05, 0.01, 0.001 respectively. Data values represent mean±SEM.

To test whether chemical inhibition of NEK6 could be used as a treatment of DPR toxicity as well, the recently described NEK6 inhibitor ZINC05007751 was tested. iCas9-hiPSC derived cortical neurons (cultured for 70-80 days) were treated with 1.75 μM to 14 μM of the inhibitor at day 1 and at day 3. The cells were subjected to a PR20 treatment (1.5 μM) at day 3 together with the compound. Axonal transport measurements were performed at day 4. In contrast to the control, the NEK6 inhibitor overruled the axonal transport defects induced by administration of PR20 to normal donor neuronal progeny (FIG. 11).

Figure 14:
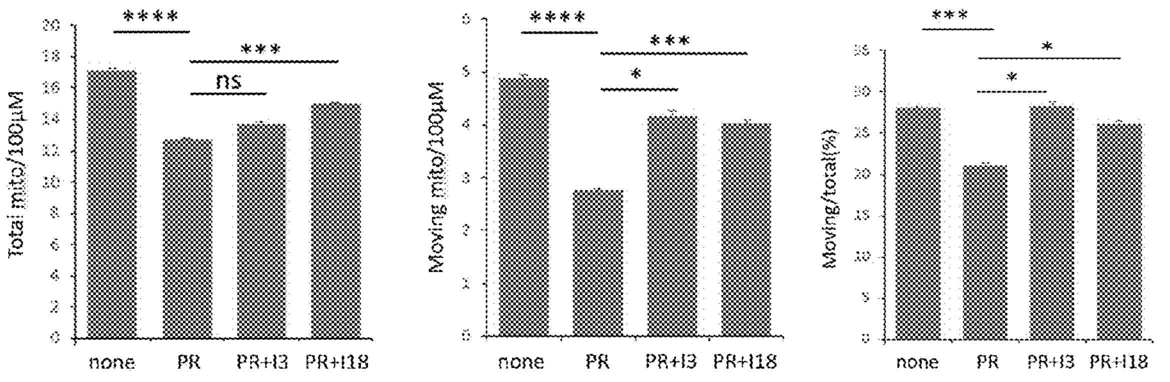
FIG. 14 shows the quantification of total mitochondria (left), moving mitochondria (middle) and ratio of moving to total mitochondria (right) normalized to a neurite length of 100 m in hiPSC-derived cortical neurons treated with PR20 peptides (PR) and the NEK6 inhibitor I-3 (PR+I3) or I–18 (PR+I18) which were added 3 days before PR20 treatment and a second time together with the PR20 treatment. Compounds I-3 and I-18 were added at 200 nM and 300 nM respectively. One-way ANOVA with post-hoc Tukey's test.

The same experiments are performed with the NEK6 inhibitors ZINC05007751 and with the NEK6 inhibitors described in WO2019126696A1. Interestingly, a treatment of 200 nm I-3 or 300 nm I-18 statistically significantly rescues the axonal transport defects observed upon PR-treatment. Both the number of moving mitochondria as the ratio of moving mitochondria to total amount of mitochondria were statistically significantly improved (FIG. 14). Also for I-18 treatment, the number of total mitochondria was statistically significantly increased compared to the a PR-treatment alone (FIG. 14).

Example 5. NEK6 as Biomarker for C9Orf72

Figure 12:
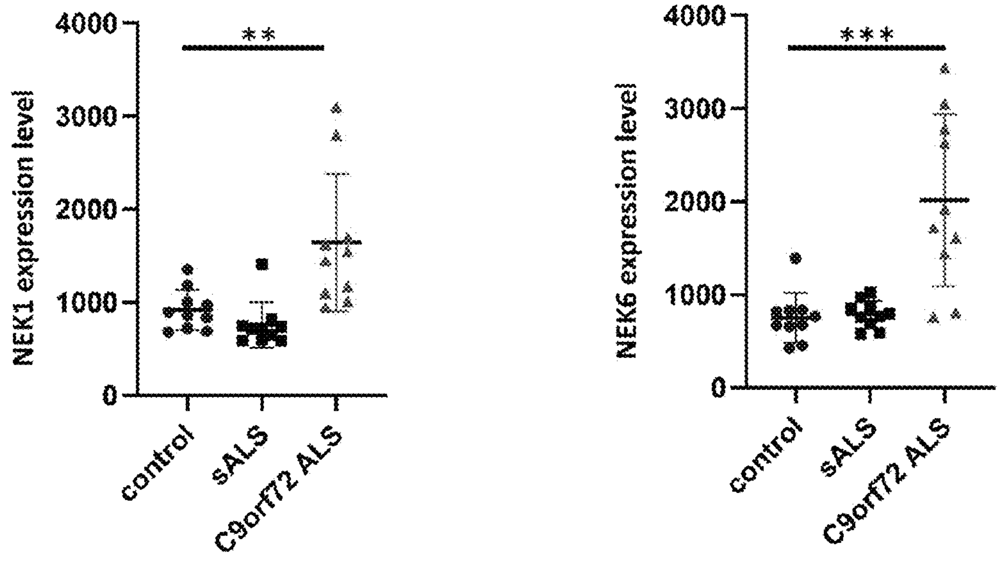
FIG. 12 shows NEK1 (left) and NEK6 (right) expression quantified by qRT-PCR in PBMC samples of healthy donors (control, n=10), sporadic ALS patients without known mutations (sALS, n=10) and ALS patients carrying C9orf72 mutation (C9orf72 ALS, n=10). One-way ANOVA with post-hoc Tukey's test, , * represent p-values of 0.01, 0.001 respectively. Data values represent mean±SEM.

We observed a significant upregulation of both NEK1 and NEK6 mRNA expression in peripheral blood mononuclear cell (PBMC) samples from 10 ALS patients carrying C9orf72 repeat expansions compared to 10 healthy controls and 10 sporadic ALS patients (FIG. 12). By contrast, a close NEK family member, NEK7, was not differently expressed in C9orf72 ALS patient blood cells (data not shown).

Example 6. SNRK Downregulation Rescues DPR Toxicity

Figure 13:
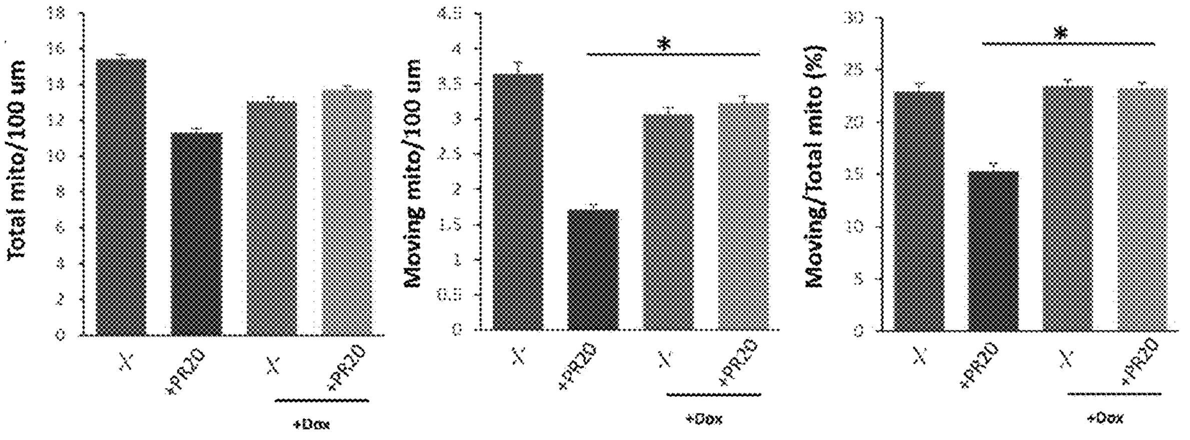
FIG. 13 shows the quantification of total mitochondria (left), moving mitochondria (middle) and the ratio of moving to total mitochondria (right) normalized to a neurite length of 100 m during a time period of 200 s in Cas9-hiPSC derived cortical neurons transduced with SNRK sgRNA, with and without PR20 treatment and treated (+Dox) or not treated with doxycycline. One-way ANOVA with post-hoc Tukey's test, * represents p-value of 0.05. Data values represent mean±SEM.

Next to NEK6-specific ASOs, also SNRK downregulation was tested as treatment for DPR toxicity. SNRK knockdown by sgRNAs in iCas9-iPSC neuronal progeny treated the PR20 induced axonal transport defects (FIG. 13), in a similar way as NEK6 sgRNAs did.

Methods

Induced Pluripotent Stem Cells and Culture

All hiPSCs were maintained on Corning Matrigel Matrix (734-0269, Corning) in Essential 8TM medium (A1517001, Gibco™) with 1000 U/ml penicillin-streptomycin. Colonies were routinely passaged with 0.5 mM EDTA (15575-020, Invitrogen) in Dulbecco's phosphate-buffered saline (DPBS). Cultures were routinely analyzed by PCR for *mycoplasma* contamination. All studies using human iPSCs were approved by the Human Ethics committee at the University Hospital, Gasthuisberg, KU Leuven, Belgium.

Recombinase-Mediated Cassette Exchange of the Inducible Cas9 Sequence in iPSCs

As described in Ordovas et al (2015 Stem Cell reports 5: 918-931), an FRT-flanked donor cassette had previously been inserted into the AAVS1 locus of BJ1 and Sigma IPSC00028 cells. Here we used recombinase-mediated cassette exchange to establish the iCas9 hiPSCs. The Cas9 cDNAs were purchased from OriGene Technologies (Rockville, USA). G418 (100 μg/ml) and 0.5 M1-(2-deoxy-2-fluoro-beta-D-arabinofuranosyl)-5-iodouracil (FIAU) were used to select for correctly recombined colonies. Correct integration of the cassette was demonstrated by 3' and 5' junction assay PCR. In addition, we used digital droplet PCR to demonstrate that only 1 cassette was present in the cells. Other QC studies were performed as described previously in Ordovas et al (2015 Stem Cell reports 5: 918-931).

Digital Droplet PCR

Genomic DNA was isolated using a DNeasy kit (Qiagen) and sequencing was performed by LGC Genomics (Berlin, Germany). HAEIII restriction enzyme (New England Biolabs) was used for the random digestion of the genomic DNAs for 2 hours. Cas9 probe were designed in house and synthesized in IDT (Germany). AP3B1 probe (dHsaCP1000001 Bio-rad) and eGFP probe (Mr00660654_cn ThermoFisher Scientific) are commercially available and were used as the reference gene. Bio-Rad ddPCR mix was used for PCR amplification. PCR mix were loaded into individual wells of disposable droplet generator cartridge (Bio-Rad). QX200 droplet generator (Bio-Rad) was used for generating droplets. Once droplets were generated, a thermal cycler was used for the PCR reaction (40 cycles). Finally, the PCR plates were read by a QX200 droplet reader (Bio-Rad).

Differentiation of Cortical Neurons from iPSCs

Cortical neurons were generated based on the Shi et al protocol (Nat. Protoc. 7, 1836-1846 (2012)). The hiPSCs were replated at high density (2.5 million cells per well of a 6 well plate) in mTESR1 medium spiked with Revitacell (1:100) (Life Technologies) or 10 μM Y-27632 (STEMCELL Technologies). Neuronal induction started when the cells reach reached confluency (>80%). NPCs were generated using dual SMAD inhibition (10 mM SB431542 (Tocris) and 1 mM LDN193189 (Miltenyi Biotec)), and rosettes purified by sequential dispase and accutase steps. DIV31-33 NPCs were cryopreserved. For final differentiation, NPCs were thawed, and cultured in N2B27 medium (Life Technologies) for a few days, and replated at 15-25.000 cells per $cm^2$ on poly-ornithine and laminin-coated plastic dishes in N2B27 medium and maintained until DIV70-DIV90 with partial medium changes twice a week.

RT/Real-Time PCR

Total RNA of hiPSC-derived cortical neurons and zebrafish embryos (at 30 hpf) were isolated by using the RNeasy kit (Qiagen) and reverse transcription was performed using SuperScript III First-Strand Synthesis SuperMix (Invitrogen) for both qRT-PCR and RT-PCR. qRT-PCR was performed using SYBR Green PCR Master Mix (Applied Biosystems) on the 7500 Step OnePlus Real-Time PCR System (Applied Biosystems). All samples were run in triplicate and relative quantification was done using the AACt method with normalization to reference genes. RT-PCR was performed by using a 96-well thermal cycler (Thermo Fisher Scientific) with optimized program. RT-PCR was done using DreamTaq Green Master Mix (Thermo Fisher Scientific), according to the manufacturer's instructions. RT-PCR reactions were analyzed on a 2% agarose gel and visualized by MIDORI Green staining (Nippon Genetics). For hiPSC-derived cortical neurons, NEK6 RT-primer set was purchased from Santa Cruz (sc-61172-PR). Cas9 real-time primers was purchased from System Biosciences (CAS9-PR-1-SBI). For zebrafish, the nek6 and gapdh RT-primers were designed in house and synthesized by IDT (Integrated DNA Technologies). A list of primers can be found in Table 1.

CRISPR/Cas Interference Screen

The Brunello kinome-wide CRISPR/Cas9 KO library (3052 sgRNAs against 736 kinases, 4 sgRNA per gene) was purchased from Addgene (1000000082). The quality control of library and lentivirus packing was performed by Vector builder (VectorBuilder GmbH, Germany). About 8 million NPCs at day 46 (DIV46 NPCs) per condition were transduced with the library at an MOI=0.3, and with a coverage of >800 cells/sgRNA. Transduced cells underwent puromycin (1 μg/ml) selection for 1 week. Cells were maintained in culture until DIV60, and then replated on poly-o-laminin coated plates at 50 000 cells/$cm^2$. On DIV70, 50% of the wells were treated with Doxycycline (3 μg/ml) with a daily medium change including Doxycycline until DIV77. At DIV79, PR20 (add 6 μg/ml; Pepscan Presto BV, The Netherlands) was added to the culture medium to 50% of the culture. After 24 hours, culture wells were washed to remove the dead cells, and cells were harvested and frozen at −80° C. or used in downstream assays. Genomic DNA was extracted from all conditions separately using the Midi Blood DNA extraction kit (51185, QIAGEN). The fragments containing sgRNAs were amplified by PCR and subsequently used for NGS on an Illumina Nextseq platform to identify the barcodes of each sgRNA present. The bioinformatics tool MAGecK 0.5.724 was used for downstream analysis. First, sgRNAs were counted using "mageck count" directly from the sequencing fastq files. We then performed maximum-likelihood analysis of gene essentialities using "mageck mle" with the default parameters and using the library of 100 non-targeting guides as parameter for controlsgRNA.

(Full processing pipeline available on world wide web at github.com/emc2cube/Bioinformatics). The enrichment of individual sgRNAs was calculated as log ratio, and gene level effects were calculated from 4 sgRNA targeting each gene. A p-value based confidence score was then derived as log-likelihood ratio describing the significance of the gene level effects. Gene ontology analysis was performed using the Gene Ontology Resource website.

Unassisted Delivery of ASOs

Locked Nucleic Acid oligonucleotides for NEK6 and SNRK were purchased from Exiqon (Vedbaek, Denmark). DIV72 iPSC-derived cortical neurons were incubated with the LNAs, dissolved in sterilized water, at a final concentration of 50 nM for 1 week prior to axonal transport analysis or other downstream analyses.

Cell Viability Test

Resazurin (R7017, Sigma) was added to the cells in neuron maintenance medium (NMM) at a concentration of 1 μg/ml. Cells were incubated for 1 h in 37° C. with 5% CO2. Absorbance was evaluated using 540 nm excitation and 590 nm emission settings.

Axonal Transport Analysis

DIV79-DIV84 iPSC-derived cortical neurons were loaded with MitoTracker-Red (50 nM, Invitrogen), washed and left to equilibrate (20 min) in NMM, before transferring them to a HEPES buffered salt solution (pH 7.4, 150 mM NaCl, 5 mM KCl, 1 mM MgCl2, 2 mM CaCl2), 10 mM glucose, 10 mM HEPES). Measurements were performed on an inverted Zeiss Axiovert 200 μM microscope (Carl Zeiss) with a 40× water immersion lens. Neurons were selected under differential interference optics (DIC) based on typical morphology consisting of a soma and long-extended neurites. MitoTracker-RED was excited at 580 nm, using a TILL Poly V light source (TILL Photonics) and image sequences were recorded (200 images at 1 Hz) onto a cooled CCD camera (PCO Sensicam-QE) using TillVisION (TILL Photonics) software. A heated gravityfed perfusion system was used to keep cells at 36±0.5° C. during the recordings. All image analysis was performed in Igor Pro (Wavemetrics) using custom written routines based on a previously described analysis algorithm (Vanden Berghe 2004 Am. J. Physiol. Gastrointest. Liver Physiol. 286, G671-G682). In brief, kymographs or spatio-temporal maps were constructed for each of the neuronal processes. In these maps, stationary mitochondria appear as vertical lines and moving mitochondria generate tilted lines. Proportions of moving and stationary mitochondria were extracted from the maps by marking and analyzing the properties of each of the mitochondrial trajectories.

Immunofluorescence Staining

For immunofluorescence analysis, cells plated on cover-slips were fixed in 4% paraformaldehyde for 20 min at room temperature, and then washed with PBS. Permeabilization was done for 30 min and blocking was done for 1 h using PBS containing 0.2% Triton X-100 (Acros Organics) and 5% donkey serum (Sigma). Cells were incubated overnight at 4° C. in blocking buffer (2% donkey serum) containing the different primary antibodies (Abs). After washing with PBS, cells were incubated with secondary antibodies (Invitrogen) for 1 h at room temperature. Fluorescent and bright field micrographs were captured using a Zeiss Axio Imager M1 microscope (Carl Zeiss) equipped with an AxioCam MRc5 (bright field, Carl Zeiss) or a monochrome AxioCam Mrm camera (fluorescence, Carl Zeiss).

Western Blotting

For Western blot analysis, cells and zebrafish embryos (6 hpf) were collected on dry ice and maintained at −80° C. until further processing. Samples were hydrolyzed in RIPA buffer (containing 50 mM Tris, 150 mM NaCl, 1% (vol/vol) NP40, 0.5% sodium deoxycholate (wt/vol), 0.1% SDS (wt/vol) complemented with protease inhibitors (Complete, Roche Diagnostics, pH 7.6). Protein concentrations were determined using the microBCA kit (Thermo Fisher Scientific Inc.) according to the manufacturer's instructions. Western blotting was performed as described before (Guo et al 2017 Nat Commun 8, 861). Optical densities were determined using the integrated density measurement tool of ImageJ (NIH).

TagMan Real-Time PCR on Human Peripheral Blood Mononuclear Cells (PBMC)

Peripheral blood mononuclear cells (PBMCs) were obtained from 10 healthy individuals, 10 sporadic ALS patients without known mutations and 10 ALS patients carrying C9orf72 mutation. The mean age of patients in the three groups was similar, and the number of males and females was also similar. Total RNA was extracted from PBMCs using TRI Reagent (Sigma Aldrich/Merck) according to the manufacturer's instructions. Reverse transcription was performed as above with 1 μg RNA. All samples were processed at the same time, the resulting cDNA diluted 1:20 in nuclease-free water, and 5 μl was used for real-time PCR. Real-time PCR reactions were performed on a 384-well format using the ViiA7 (Applied Biosystems/Thermo Fisher). All assays were probe-based allowing multiplexing, the genes of interest [NEK1 (Hs01583138_ml), NEK6 (Hs01032395_ml), NEK7 (Hs00370356_ml)] and stable reference genes [HPRT (Hs02800695_m1) and RPLPO (Hs00420895_gH)](all Applied Biosystems/Thermo Fisher). The assays were validated, and PCR efficiency was 100% +/−10%. Realtime reactions were run in triplicate using TaqMan Fast Universal PCR Master Mix (2X), no AmpErase UNG (Applied Biosystems/Thermo Fisher). Collected data were analyzed using qbaseplus (Biogazelle), according to standards of the MIQE guidelines (Bustin et al 2009 Clin Chem 55, 611-622).

Zebrafish Injections, SV2 Immunohistochemistry and Phenotyping

Zebrafish work was performed as previously described in Swinnen et al (2018 Acta Neuropathol 135, 427-443). Zebrafish oocytes were injected at one-cell stage with the indicated amounts of the morpholinos. The splice-blocking morpholino against *Danio rerio* nek6 (transcript ENSDART00000132599.2; morpholino sequence 5'-ATGTTAGAAAGTGTACCTCGATGCA-3' SEQ ID NO: 4) and the standard control oligo (morpholino sequence 5'-CCTCTTACCTCAGTTACAATTTATA-3' SEQ ID NO: 5) were designed and generated by Gene Tools (Philomath, USA). Injected oocytes were incubated at 28° C. After 24 hpf, the embryos were dechorionated by using a forceps. Only morphologically normal embryos were selected for downstream experiments. At 30 hpf, the selected fish were deyolked and subsequently fixed overnight at 4° C. in 4% formaldehyde in 1× PBS. Fish were permeabilized with acetone for 1 h at −20° C., blocked with 1% BSA/1% DMSO/PBS for 1 h at room temperature and immune-stained with mouse anti-SV2 primary antibody followed by secondary antibody. For phenotyping, 15 consecutive embryos per condition were analyzed with imaging (Leica DM 3000 LED microscope; DMK 33UX250 USB3.0 monochrome industrial camera, The Imaging Source, Bremen, Germany) and the Lucia software (version 4.60, Laboratory Imaging, Prague, Czech Republic) by a blinded observer. For the axonal length, a standardized method was used; five predefined and consecutive motor axons (i.e. the 8th up to the 12th axon on one side) were measured in all 15 embryos. Data for axonal length were normalized to the control condition. For the abnormal branching, a predefined set of 20 consecutive motor axons (i.e. the 8th up to the 17th axon on both sides) in the same 15 embryos were analyzed visually. Motor axons were considered abnormal when axons branched at or before the ventral edge of the notochord. An embryo was considered as having 'abnormal branching' when at least two of these 20 axons were abnormal. For each experiment, GFP-targeting morpholino was used as control at the same dose of the tested morpholino. Four biological replicates were performed. Axonal length and abnormal branching data represent mean±95% CI. Statistical analysis was done by One-way ANOVA and logistic regression.

Proteomics

Peptides from cortical neuronal pellets were prepared as described in Tharkeshwar et al 2017 Sci Rep 7, 41408). A part (100 l) was dried completely and used for shotgun analysis, while the rest was used for phosphopeptide enrichment as described in Tharkeshwar et al (2017 Sci Rep 7, 41408). Data analysis of the shotgun and phosphoproteomics data was performed with MaxQuant (version 1.6.11.0) using the *Andromeda* search engine with default search settings. Spectra were searched against the human proteins in the Swiss-Prot Reference Proteome database (version January 2020). The mass tolerance for precursor and fragment ions was set to 4.5 and 20 ppm, while the enzyme specificity was set as C-terminal to arginine and lysine. Variable modifications were set to oxidation of methionine residues, acetylation of protein N-termini and phosphorylation of serine, threonine or tyrosine residues, while carbamidomethylation of cysteine residues was set as fixed modification. Matching between runs was enabled with a matching time window of 0.7 minutes and an alignment time window of 20 minutes. Only proteins with at least one unique or razor peptide were retained MaxLFQ algorithm integrated in the MaxQuant software was used to quantify the proteins that had a minimum ratio count of two unique or razor peptides. A two-way ANOVA test was performed to compare the intensities of the proteins in the Condition group (Ctrl vs. KD) to reveal proteins in which the expression level was significantly regulated. For each protein, this test calculated a p-value (−log p-value) for Condition. For the analysis of the phosphoproteomics data, the phospho (STY)sites file was loaded in the Perseus software (version 1.6.2.1). Reverse hits were removed, the site table was expanded, the intensity values were log 2 transformed and the median was subtracted. Replicate samples were grouped, phosphosites with less than three valid values in at least one group were removed and missing values were imputed from a normal distribution around the detection limit leading to a list of quantified phosphopeptides that was used for further data analysis. Then, t-tests were performed (FDR=0.05 and s0=1) to compare phosphopeptide intensities in the different sample types. The mass spectrometry proteomics data will be deposited to the ProteomeXchange Consortium via the PRIDE partner.

Quantification and Statistics

A minimum of three independent experiments based on three biologically different differentiations were always performed. Statistical analysis was performed using Graphpad Prism version 5.0b. One-way ANOVA was used for the other experiments with post-hoc Tukey's test to determine statistical differences between groups.*P<0.05, P<0.01, *P<0.001, ****P<0.0001 were considered significant. Data values represent mean±SEM, unless indicated otherwise.

TABLE S1

Primers for semi-quantitative RT-PCR, qPCR, sequencing, cloning related to Gene editing

| NAME | FORWARD SEQUENCE (5'-3') | REVERSE SEQUENCE (5'-3') |
|---|---|---|
| 5'JA AAVS1 | CTGCCGTCTCTCTCCTGAGTC (SEQ ID NO: 6) | TTGTGCCCAGTCATAGCCGAAT (SEQ ID NO: 7) |
| 3'JA AAVS1 | TTAGACATGCTCCCAGCCGATG (SEQ ID NO: 8) | TACCCCGAAGAGTGAGTTTGCC (SEQ ID NO: 9) |
| GFP | CTGGTCGAGCTGGACGGCGACG (SEQ ID NO: 10) | CACGAACTCCAGCAGGACCATG (SEQ ID NO: 11) |
| TIA1G1 | GGATAAATGTTGGCGTGCTT (SEQ ID NO: 12) | TACTCTGCATGCCTCAGGTG (SEQ ID NO: 13) |
| TIA1G2 | CCCAGGAGGTGGAGATTGTA (SEQ ID NO: 14) | TAGCCAACCAGTTGACACCA (SEQ ID NO: 15) |
| TIA1G3 | TGTAATGTCTGGGCAACCAA (SEQ ID NO: 16) | TGGGAAAACAATCTTTTGCTG (SEQ ID NO: 17) |
| LIN28G | AGCGGGGACACTTTAGGATT (SEQ ID NO: 18) | GGGTGCTGATAATTGGTGCT (SEQ ID NO: 19) |
| HUMAN GAPDH | ACCAGGAAATGAGCTTGACAAA (SEQ ID NO: 20) | TCAAGAAGGTGGTGAAGCAGG (SEQ ID NO: 21) |
| ZEBRAFISH NEK6 | GATGGATGCTAAAGCCAGACAGG AC (SEQ ID NO: 22) | TCAATCTTATGGCACAGCGAGA GC (SEQ ID NO: 23) |
| ZEBRAFISH GAPDH | CCCATGTTTGTCATGGGTGT (SEQ ID NO: 24) | GGTTGCTGTAACCGAACTCA (SEQ ID NO: 25) |

The invention claimed is:

1. A method to reduce axonal transport defects in a subject suffering therefrom, the method comprising: administering to the subject an effective amount of ZINCO5007751, or ZINC04384801;

wherein the administration is one of direct injection into the brain, uptake into the brain after disruption of the blood-brain barrier by pharmaceutical agent or ultrasound, or intra-arterial cerebral infusion.

2. The method according to claim 1, wherein the subject suffers from a dipeptide repeat toxicity disease.

3. The method according to claim 1, wherein the subject suffers from amyotrophic lateral sclerosis (ALS), frontotemporal dementia (FTD), or ALS with FTD.

4. The method according to claim 1, wherein the NEK6 inhibitor statistically significantly reduces the expression of NEK6 in the neurons of the subject.

5. The method of claim 1, wherein the subject suffers from C9FTD/ALS, and wherein the method further comprises:

determining the expression level of NEK6 and/or NEK1 in a sample obtained from the subject prior to treatment with the NEK6 inhibitor; and determining that the expression level of NEK6 and/or NEK1 is statistically significantly increased as compared to a subject not suffering from C9FTD/ALS; and applying an ALS treatment to the subject.

6. The method according to claim 5, wherein C9FTD/ALS is C9orf72-ALS and/or C9orf72-FTD.

7. The method according to claim 6, wherein the blood sample is a peripheral blood mononuclear cell sample.

8. The method according to claim 5, wherein the sample is a blood, serum, or plasma sample.

9. The method according to claim 5, wherein applying the ALS treatment comprises administering to the subject a medicament selected from the list consisting of edaravone, riluzole, dextromethorphan hydrobromide and quinidine sulfate, and a sodium phenylbutyrate—taurursodiol formulation.

* * * * *

SEQUENCE LISTING

<160> NUMBER OF SEQ ID NOS: 25

<210> SEQ ID NO 1
<211> LENGTH: 313
<212> TYPE: PRT
<213> ORGANISM: Homo sapiens

<400> SEQUENCE: 1

```
Met Ala Gly Gln Pro Gly His Met Pro His Gly Gly Ser Ser Asn Asn
1               5                   10                  15

Leu Cys His Thr Leu Gly Pro Val His Pro Pro Asp Pro Gln Arg His
            20                  25                  30

Pro Asn Thr Leu Ser Phe Arg Cys Ser Leu Ala Asp Phe Gln Ile Glu
        35                  40                  45
```

-continued

```
Lys Lys Ile Gly Arg Gly Gln Phe Ser Glu Val Tyr Lys Ala Thr Cys
    50                  55                  60

Leu Leu Asp Arg Lys Thr Val Ala Leu Lys Lys Val Gln Ile Phe Glu
65                  70                  75                  80

Met Met Asp Ala Lys Ala Arg Gln Asp Cys Val Lys Glu Ile Gly Leu
                85                  90                  95

Leu Lys Gln Leu Asn His Pro Asn Ile Ile Lys Tyr Leu Asp Ser Phe
            100                 105                 110

Ile Glu Asp Asn Glu Leu Asn Ile Val Leu Glu Leu Ala Asp Ala Gly
        115                 120                 125

Asp Leu Ser Gln Met Ile Lys Tyr Phe Lys Lys Gln Lys Arg Leu Ile
    130                 135                 140

Pro Glu Arg Thr Val Trp Lys Tyr Phe Val Gln Leu Cys Ser Ala Val
145                 150                 155                 160

Glu His Met His Ser Arg Arg Val Met His Arg Asp Ile Lys Pro Ala
                165                 170                 175

Asn Val Phe Ile Thr Ala Thr Gly Val Val Lys Leu Gly Asp Leu Gly
            180                 185                 190

Leu Gly Arg Phe Phe Ser Ser Glu Thr Thr Ala Ala His Ser Leu Val
        195                 200                 205

Gly Thr Pro Tyr Tyr Met Ser Pro Glu Arg Ile His Glu Asn Gly Tyr
    210                 215                 220

Asn Phe Lys Ser Asp Ile Trp Ser Leu Gly Cys Leu Leu Tyr Glu Met
225                 230                 235                 240

Ala Ala Leu Gln Ser Pro Phe Tyr Gly Asp Lys Met Asn Leu Phe Ser
                245                 250                 255

Leu Cys Gln Lys Ile Glu Gln Cys Asp Tyr Pro Pro Leu Pro Gly Glu
            260                 265                 270

His Tyr Ser Glu Lys Leu Arg Glu Leu Val Ser Met Cys Ile Cys Pro
        275                 280                 285

Asp Pro His Gln Arg Pro Asp Ile Gly Tyr Val His Gln Val Ala Lys
    290                 295                 300

Gln Met His Ile Trp Met Ser Ser Thr
305                 310


<210> SEQ ID NO 2
<211> LENGTH: 765
<212> TYPE: PRT
<213> ORGANISM: Homo sapiens

<400> SEQUENCE: 2

Met Ala Gly Phe Lys Arg Gly Tyr Asp Gly Lys Ile Ala Gly Leu Tyr
1               5                   10                  15

Asp Leu Asp Lys Thr Leu Gly Arg Gly His Phe Ala Val Val Lys Leu
            20                  25                  30

Ala Arg His Val Phe Thr Gly Glu Lys Val Ala Val Lys Val Ile Asp
        35                  40                  45

Lys Thr Lys Leu Asp Thr Leu Ala Thr Gly His Leu Phe Gln Glu Val
    50                  55                  60

Arg Cys Met Lys Leu Val Gln His Pro Asn Ile Val Arg Leu Tyr Glu
65                  70                  75                  80

Val Ile Asp Thr Gln Thr Lys Leu Tyr Leu Ile Leu Glu Leu Gly Asp
                85                  90                  95

Gly Gly Asp Met Phe Asp Tyr Ile Met Lys His Glu Glu Gly Leu Asn
```

-continued

```
            100                 105                 110

Glu Asp Leu Ala Lys Lys Tyr Phe Ala Gln Ile Val His Ala Ile Ser
        115                 120                 125

Tyr Cys His Lys Leu His Val Val His Arg Asp Leu Lys Pro Glu Asn
    130                 135                 140

Val Val Phe Phe Glu Lys Gln Gly Leu Val Lys Leu Thr Asp Phe Gly
145                 150                 155                 160

Phe Ser Asn Lys Phe Gln Pro Gly Lys Lys Leu Thr Thr Ser Cys Gly
                165                 170                 175

Ser Leu Ala Tyr Ser Ala Pro Glu Ile Leu Leu Gly Asp Glu Tyr Asp
            180                 185                 190

Ala Pro Ala Val Asp Ile Trp Ser Leu Gly Val Ile Leu Phe Met Leu
        195                 200                 205

Val Cys Gly Gln Pro Pro Phe Gln Glu Ala Asn Asp Ser Glu Thr Leu
    210                 215                 220

Thr Met Ile Met Asp Cys Lys Tyr Thr Val Pro Ser His Val Ser Lys
225                 230                 235                 240

Glu Cys Lys Asp Leu Ile Thr Arg Met Leu Gln Arg Asp Pro Lys Arg
                245                 250                 255

Arg Ala Ser Leu Glu Glu Ile Glu Asn His Pro Trp Leu Gln Gly Val
            260                 265                 270

Asp Pro Ser Pro Ala Thr Lys Tyr Asn Ile Pro Leu Val Ser Tyr Lys
        275                 280                 285

Asn Leu Ser Glu Glu Glu His Asn Ser Ile Ile Gln Arg Met Val Leu
    290                 295                 300

Gly Asp Ile Ala Asp Arg Asp Ala Ile Val Glu Ala Leu Glu Thr Asn
305                 310                 315                 320

Arg Tyr Asn His Ile Thr Ala Thr Tyr Phe Leu Leu Ala Glu Arg Ile
                325                 330                 335

Leu Arg Glu Lys Gln Glu Lys Glu Ile Gln Thr Arg Ser Ala Ser Pro
            340                 345                 350

Ser Asn Ile Lys Ala Gln Phe Arg Gln Ser Trp Pro Thr Lys Ile Asp
        355                 360                 365

Val Pro Gln Asp Leu Glu Asp Asp Leu Thr Ala Thr Pro Leu Ser His
    370                 375                 380

Ala Thr Val Pro Gln Ser Pro Ala Arg Ala Ala Asp Ser Val Leu Asn
385                 390                 395                 400

Gly His Arg Ser Lys Gly Leu Cys Asp Ser Ala Lys Lys Asp Asp Leu
                405                 410                 415

Pro Glu Leu Ala Gly Pro Ala Leu Ser Thr Val Pro Pro Ala Ser Leu
            420                 425                 430

Lys Pro Thr Ala Ser Gly Arg Lys Cys Leu Phe Arg Val Glu Glu Asp
        435                 440                 445

Glu Glu Glu Asp Glu Glu Asp Lys Lys Pro Met Ser Leu Ser Thr Gln
    450                 455                 460

Val Val Leu Arg Arg Lys Pro Ser Val Thr Asn Arg Leu Thr Ser Arg
465                 470                 475                 480

Lys Ser Ala Pro Val Leu Asn Gln Ile Phe Glu Glu Gly Glu Ser Asp
                485                 490                 495

Asp Glu Phe Asp Met Asp Glu Asn Leu Pro Pro Lys Leu Ser Arg Leu
            500                 505                 510

Lys Met Asn Ile Ala Ser Pro Gly Thr Val His Lys Arg Tyr His Arg
        515                 520                 525
```

```
Arg Lys Ser Gln Gly Arg Gly Ser Ser Cys Ser Ser Ser Glu Thr Ser
    530                 535                 540

Asp Asp Asp Ser Glu Ser Arg Arg Arg Leu Asp Lys Asp Ser Gly Phe
545                 550                 555                 560

Thr Tyr Ser Trp His Arg Arg Asp Ser Ser Glu Gly Pro Pro Gly Ser
                565                 570                 575

Glu Gly Asp Gly Gly Gly Gln Ser Lys Pro Ser Asn Ala Ser Gly Gly
            580                 585                 590

Val Asp Lys Ala Ser Pro Ser Glu Asn Asn Ala Gly Gly Gly Ser Pro
        595                 600                 605

Ser Ser Gly Ser Gly Gly Asn Pro Thr Asn Thr Ser Gly Thr Thr Arg
    610                 615                 620

Arg Cys Ala Gly Pro Ser Asn Ser Met Gln Leu Ala Ser Arg Ser Ala
625                 630                 635                 640

Gly Glu Leu Val Glu Ser Leu Lys Leu Met Ser Leu Cys Leu Gly Ser
                645                 650                 655

Gln Leu His Gly Ser Thr Lys Tyr Ile Ile Asp Pro Gln Asn Gly Leu
            660                 665                 670

Ser Phe Ser Ser Val Lys Val Gln Glu Lys Ser Thr Trp Lys Met Cys
        675                 680                 685

Ile Ser Ser Thr Gly Asn Ala Gly Gln Val Pro Ala Val Gly Gly Ile
    690                 695                 700

Lys Phe Phe Ser Asp His Met Ala Asp Thr Thr Thr Glu Leu Glu Arg
705                 710                 715                 720

Ile Lys Ser Lys Asn Leu Lys Asn Asn Val Leu Gln Leu Pro Leu Cys
                725                 730                 735

Glu Lys Thr Ile Ser Val Asn Ile Gln Arg Asn Pro Lys Glu Gly Leu
            740                 745                 750

Leu Cys Ala Ser Ser Pro Ala Ser Cys Cys His Val Ile
        755                 760                 765


<210> SEQ ID NO 3
<211> LENGTH: 1258
<212> TYPE: PRT
<213> ORGANISM: Homo sapiens

<400> SEQUENCE: 3

Met Glu Lys Tyr Val Arg Leu Gln Lys Ile Gly Glu Gly Ser Phe Gly
1               5                   10                  15

Lys Ala Ile Leu Val Lys Ser Thr Glu Asp Gly Arg Gln Tyr Val Ile
            20                  25                  30

Lys Glu Ile Asn Ile Ser Arg Met Ser Ser Lys Glu Arg Glu Glu Ser
        35                  40                  45

Arg Arg Glu Val Ala Val Leu Ala Asn Met Lys His Pro Asn Ile Val
    50                  55                  60

Gln Tyr Arg Glu Ser Phe Glu Glu Asn Gly Ser Leu Tyr Ile Val Met
65                  70                  75                  80

Asp Tyr Cys Glu Gly Gly Asp Leu Phe Lys Arg Ile Asn Ala Gln Lys
                85                  90                  95

Gly Val Leu Phe Gln Glu Asp Gln Ile Leu Asp Trp Phe Val Gln Ile
            100                 105                 110

Cys Leu Ala Leu Lys His Val His Asp Arg Lys Ile Leu His Arg Asp
        115                 120                 125

Ile Lys Ser Gln Asn Ile Phe Leu Thr Lys Asp Gly Thr Val Gln Leu
```

-continued

```
    130                 135                 140

Gly Asp Phe Gly Ile Ala Arg Val Leu Asn Ser Thr Val Glu Leu Ala
145                 150                 155                 160

Arg Thr Cys Ile Gly Thr Pro Tyr Tyr Leu Ser Pro Glu Ile Cys Glu
                165                 170                 175

Asn Lys Pro Tyr Asn Asn Lys Ser Asp Ile Trp Ala Leu Gly Cys Val
            180                 185                 190

Leu Tyr Glu Leu Cys Thr Leu Lys His Ala Phe Glu Ala Gly Ser Met
        195                 200                 205

Lys Asn Leu Val Leu Lys Ile Ile Ser Gly Ser Phe Pro Pro Val Ser
    210                 215                 220

Leu His Tyr Ser Tyr Asp Leu Arg Ser Leu Val Ser Gln Leu Phe Lys
225                 230                 235                 240

Arg Asn Pro Arg Asp Arg Pro Ser Val Asn Ser Ile Leu Glu Lys Gly
                245                 250                 255

Phe Ile Ala Lys Arg Ile Glu Lys Phe Leu Ser Pro Gln Leu Ile Ala
            260                 265                 270

Glu Glu Phe Cys Leu Lys Thr Phe Ser Lys Phe Gly Ser Gln Pro Ile
        275                 280                 285

Pro Ala Lys Arg Pro Ala Ser Gly Gln Asn Ser Ile Ser Val Met Pro
    290                 295                 300

Ala Gln Lys Ile Thr Lys Pro Ala Ala Lys Tyr Gly Ile Pro Leu Ala
305                 310                 315                 320

Tyr Lys Lys Tyr Gly Asp Lys Lys Leu His Glu Lys Lys Pro Leu Gln
                325                 330                 335

Lys His Lys Gln Ala His Gln Thr Pro Glu Lys Arg Val Asn Thr Gly
            340                 345                 350

Glu Glu Arg Arg Lys Ile Ser Glu Glu Ala Ala Arg Lys Arg Arg Leu
        355                 360                 365

Glu Phe Ile Glu Lys Glu Lys Lys Gln Lys Asp Gln Ile Ile Ser Leu
    370                 375                 380

Met Lys Ala Glu Gln Met Lys Arg Gln Glu Lys Glu Arg Leu Glu Arg
385                 390                 395                 400

Ile Asn Arg Ala Arg Glu Gln Gly Trp Arg Asn Val Leu Ser Ala Gly
                405                 410                 415

Gly Ser Gly Glu Val Lys Ala Pro Phe Leu Gly Ser Gly Gly Thr Ile
            420                 425                 430

Ala Pro Ser Ser Phe Ser Ser Arg Gly Gln Tyr Glu His Tyr His Ala
        435                 440                 445

Ile Phe Asp Gln Met Gln Gln Gln Arg Ala Glu Asp Asn Glu Ala Lys
    450                 455                 460

Trp Lys Arg Glu Ile Tyr Gly Arg Gly Leu Pro Glu Arg Gly Ile Leu
465                 470                 475                 480

Pro Gly Val Arg Pro Gly Phe Pro Tyr Gly Ala Ala Gly His His His
                485                 490                 495

Phe Pro Asp Ala Asp Asp Ile Arg Lys Thr Leu Lys Arg Leu Lys Ala
            500                 505                 510

Val Ser Lys Gln Ala Asn Ala Asn Arg Gln Lys Gly Gln Leu Ala Val
        515                 520                 525

Glu Arg Ala Lys Gln Val Glu Glu Phe Leu Gln Arg Lys Arg Glu Ala
    530                 535                 540

Met Gln Asn Lys Ala Arg Ala Glu Gly His Met Val Tyr Leu Ala Arg
545                 550                 555                 560
```

-continued

Leu Arg Gln Ile Arg Leu Gln Asn Phe Asn Glu Arg Gln Gln Ile Lys
565 570 575

Ala Lys Leu Arg Gly Glu Lys Lys Glu Ala Asn His Ser Glu Gly Gln
580 585 590

Glu Gly Ser Glu Glu Ala Asp Met Arg Arg Lys Lys Ile Glu Ser Leu
595 600 605

Lys Ala His Ala Asn Ala Arg Ala Ala Val Leu Lys Glu Gln Leu Glu
610 615 620

Arg Lys Arg Lys Glu Ala Tyr Glu Arg Glu Lys Lys Val Trp Glu Glu
625 630 635 640

His Leu Val Ala Lys Gly Val Lys Ser Ser Asp Val Ser Pro Pro Leu
645 650 655

Gly Gln His Glu Thr Gly Gly Ser Pro Ser Lys Gln Gln Met Arg Ser
660 665 670

Val Ile Ser Val Thr Ser Ala Leu Lys Glu Val Gly Val Asp Ser Ser
675 680 685

Leu Thr Asp Thr Arg Glu Thr Ser Glu Glu Met Gln Lys Thr Asn Asn
690 695 700

Ala Ile Ser Ser Lys Arg Glu Ile Leu Arg Arg Leu Asn Glu Asn Leu
705 710 715 720

Lys Ala Gln Glu Asp Glu Lys Gly Lys Gln Asn Leu Ser Asp Thr Phe
725 730 735

Glu Ile Asn Val His Glu Asp Ala Lys Glu His Glu Lys Glu Lys Ser
740 745 750

Val Ser Ser Asp Arg Lys Lys Trp Glu Ala Gly Gly Gln Leu Val Ile
755 760 765

Pro Leu Asp Glu Leu Thr Leu Asp Thr Ser Phe Ser Thr Thr Glu Arg
770 775 780

His Thr Val Gly Glu Val Ile Lys Leu Gly Pro Asn Gly Ser Pro Arg
785 790 795 800

Arg Ala Trp Gly Lys Ser Pro Thr Asp Ser Val Leu Lys Ile Leu Gly
805 810 815

Glu Ala Glu Leu Gln Leu Gln Thr Glu Leu Leu Glu Asn Thr Thr Ile
820 825 830

Arg Ser Glu Ile Ser Pro Glu Gly Glu Lys Tyr Lys Pro Leu Ile Thr
835 840 845

Gly Glu Lys Lys Val Gln Cys Ile Ser His Glu Ile Asn Pro Ser Ala
850 855 860

Ile Val Asp Ser Pro Val Glu Thr Lys Ser Pro Glu Phe Ser Glu Ala
865 870 875 880

Ser Pro Gln Met Ser Leu Lys Leu Glu Gly Asn Leu Glu Glu Pro Asp
885 890 895

Asp Leu Glu Thr Glu Ile Leu Gln Glu Pro Ser Gly Thr Asn Lys Asp
900 905 910

Glu Ser Leu Pro Cys Thr Ile Thr Asp Val Trp Ile Ser Glu Glu Lys
915 920 925

Glu Thr Lys Glu Thr Gln Ser Ala Asp Arg Ile Thr Ile Gln Glu Asn
930 935 940

Glu Val Ser Glu Asp Gly Val Ser Ser Thr Val Asp Gln Leu Ser Asp
945 950 955 960

Ile His Ile Glu Pro Gly Thr Asn Asp Ser Gln His Ser Lys Cys Asp
965 970 975

-continued

```
Val Asp Lys Ser Val Gln Pro Glu Pro Phe Phe His Lys Val Val His
            980                 985                 990

Ser Glu His Leu Asn Leu Val Pro  Gln Val Gln Ser Val  Gln Cys Ser
        995                 1000                 1005

Pro Glu  Glu Ser Phe Ala Phe  Arg Ser His Ser His  Leu Pro Pro
    1010                 1015                 1020

Lys Asn  Lys Asn Lys Asn Ser  Leu Leu Ile Gly Leu  Ser Thr Gly
    1025                 1030                 1035

Leu Phe  Asp Ala Asn Asn Pro  Lys Met Leu Arg Thr  Cys Ser Leu
    1040                 1045                 1050

Pro Asp  Leu Ser Lys Leu Phe  Arg Thr Leu Met Asp  Val Pro Thr
    1055                 1060                 1065

Val Gly  Asp Val Arg Gln Asp  Asn Leu Glu Ile Asp  Glu Ile Glu
    1070                 1075                 1080

Asp Glu  Asn Ile Lys Glu Gly  Pro Ser Asp Ser Glu  Asp Ile Val
    1085                 1090                 1095

Phe Glu  Glu Thr Asp Thr Asp  Leu Gln Glu Leu Gln  Ala Ser Met
    1100                 1105                 1110

Glu Gln  Leu Leu Arg Glu Gln  Pro Gly Glu Glu Tyr  Ser Glu Glu
    1115                 1120                 1125

Glu Glu  Ser Val Leu Lys Asn  Ser Asp Val Glu Pro  Thr Ala Asn
    1130                 1135                 1140

Gly Thr  Asp Val Ala Asp Glu  Asp Asp Asn Pro Ser  Ser Glu Ser
    1145                 1150                 1155

Ala Leu  Asn Glu Glu Trp His  Ser Asp Asn Ser Asp  Gly Glu Ile
    1160                 1165                 1170

Ala Ser  Glu Cys Glu Cys Asp  Ser Val Phe Asn His  Leu Glu Glu
    1175                 1180                 1185

Leu Arg  Leu His Leu Glu Gln  Glu Met Gly Phe Glu  Lys Phe Phe
    1190                 1195                 1200

Glu Val  Tyr Glu Lys Ile Lys  Ala Ile His Glu Asp  Glu Asp Glu
    1205                 1210                 1215

Asn Ile  Glu Ile Cys Ser Lys  Ile Val Gln Asn Ile  Leu Gly Asn
    1220                 1225                 1230

Glu His  Gln His Leu Tyr Ala  Lys Ile Leu His Leu  Val Met Ala
    1235                 1240                 1245

Asp Gly  Ala Tyr Gln Glu Asp  Asn Asp Glu
    1250                 1255
```

<210> SEQ ID NO 4
<211> LENGTH: 25
<212> TYPE: DNA
<213> ORGANISM: Artificial Sequence
<220> FEATURE:
<223> OTHER INFORMATION: morpholino

<400> SEQUENCE: 4
atgttagaaa gtgtacctcg atgca 25

<210> SEQ ID NO 5
<211> LENGTH: 25
<212> TYPE: DNA
<213> ORGANISM: Artificial Sequence
<220> FEATURE:
<223> OTHER INFORMATION: morpholino

<400> SEQUENCE: 5

-continued

```
cctcttacct cagttacaat ttata                                          25


<210> SEQ ID NO 6
<211> LENGTH: 21
<212> TYPE: DNA
<213> ORGANISM: Artificial Sequence
<220> FEATURE:
<223> OTHER INFORMATION: primer

<400> SEQUENCE: 6

ctgccgtctc tctcctgagt c                                              21


<210> SEQ ID NO 7
<211> LENGTH: 22
<212> TYPE: DNA
<213> ORGANISM: Artificial Sequence
<220> FEATURE:
<223> OTHER INFORMATION: primer

<400> SEQUENCE: 7

ttgtgcccag tcatagccga at                                             22


<210> SEQ ID NO 8
<211> LENGTH: 22
<212> TYPE: DNA
<213> ORGANISM: Artificial Sequence
<220> FEATURE:
<223> OTHER INFORMATION: primer

<400> SEQUENCE: 8

ttagacatgc tcccagccga tg                                             22


<210> SEQ ID NO 9
<211> LENGTH: 22
<212> TYPE: DNA
<213> ORGANISM: Artificial Sequence
<220> FEATURE:
<223> OTHER INFORMATION: Primer

<400> SEQUENCE: 9

taccccgaag agtgagtttg cc                                             22


<210> SEQ ID NO 10
<211> LENGTH: 22
<212> TYPE: DNA
<213> ORGANISM: Artificial Sequence
<220> FEATURE:
<223> OTHER INFORMATION: primer

<400> SEQUENCE: 10

ctggtcgagc tggacggcga cg                                             22


<210> SEQ ID NO 11
<211> LENGTH: 22
<212> TYPE: DNA
<213> ORGANISM: Artificial Sequence
<220> FEATURE:
<223> OTHER INFORMATION: primer

<400> SEQUENCE: 11

cacgaactcc agcaggacca tg                                             22


<210> SEQ ID NO 12
<211> LENGTH: 20
<212> TYPE: DNA
<213> ORGANISM: Artificial Sequence
```

<220> FEATURE:
<223> OTHER INFORMATION: primer

<400> SEQUENCE: 12
ggataaatgt tggcgtgctt 20

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
tactctgcat gcctcaggtg 20

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
cccaggaggt ggagattgta 20

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
tagccaacca gttgacacca 20

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
tgtaatgtct gggcaaccaa 20

<210> SEQ ID NO 17
<211> LENGTH: 21
<212> TYPE: DNA
<213> ORGANISM: Artificial Sequence
<220> FEATURE:
<223> OTHER INFORMATION: primer

<400> SEQUENCE: 17
tgggaaaaca atcttttgct g 21

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
agcggggaca ctttaggatt 20

-continued

<210> SEQ ID NO 19
<211> LENGTH: 20
<212> TYPE: DNA
<213> ORGANISM: Artificial Sequence
<220> FEATURE:
<223> OTHER INFORMATION: primer

<400> SEQUENCE: 19
gggtgctgat aattggtgct 20

<210> SEQ ID NO 20
<211> LENGTH: 22
<212> TYPE: DNA
<213> ORGANISM: Artificial Sequence
<220> FEATURE:
<223> OTHER INFORMATION: primer

<400> SEQUENCE: 20
accaggaaat gagcttgaca aa 22

<210> SEQ ID NO 21
<211> LENGTH: 21
<212> TYPE: DNA
<213> ORGANISM: Artificial Sequence
<220> FEATURE:
<223> OTHER INFORMATION: primer

<400> SEQUENCE: 21
tcaagaaggt ggtgaagcag g 21

<210> SEQ ID NO 22
<211> LENGTH: 25
<212> TYPE: DNA
<213> ORGANISM: Artificial Sequence
<220> FEATURE:
<223> OTHER INFORMATION: primer

<400> SEQUENCE: 22
gatggatgct aaagccagac aggac 25

<210> SEQ ID NO 23
<211> LENGTH: 24
<212> TYPE: DNA
<213> ORGANISM: Artificial Sequence
<220> FEATURE:
<223> OTHER INFORMATION: primer

<400> SEQUENCE: 23
tcaatcttat ggcacagcga gagc 24

<210> SEQ ID NO 24
<211> LENGTH: 20
<212> TYPE: DNA
<213> ORGANISM: Artificial Sequence
<220> FEATURE:
<223> OTHER INFORMATION: primer

<400> SEQUENCE: 24
cccatgtttg tcatgggtgt 20

<210> SEQ ID NO 25
<211> LENGTH: 20
<212> TYPE: DNA
<213> ORGANISM: Artificial Sequence
<220> FEATURE:
<223> OTHER INFORMATION: primer -continued

<400> SEQUENCE: 25
ggttgctgta accgaactca 20